United States Patent [19]

Felgner et al.

[11] Patent Number: 6,165,720
[45] Date of Patent: Dec. 26, 2000

[54] CHEMICAL MODIFICATION OF DNA USING PEPTIDE NUCLEIC ACID CONJUGATES

[75] Inventors: Philip L. Felgner, Rancho Santa Fe; Olivier Zelphati, La Jolla; C. Frank Bennett, Carlsbad, all of Calif.

[73] Assignees: Gene Therapy Systems, San Diego; Isis Pharmaceuticals, Inc., Carlsbad, both of Calif.

[21] Appl. No.: 09/224,818

[22] Filed: Dec. 30, 1998

Related U.S. Application Data

[63] Continuation of application No. 09/087,815, May 29, 1998, abandoned.
[60] Provisional application No. 60/059,215, Sep. 18, 1997.
[51] Int. Cl.$^7$ .............................. C12Q 1/64; C12N 15/63; C07H 21/00
[52] U.S. Cl. .......................... 435/6; 435/320.1; 435/455; 536/22.1; 536/23.1; 536/24.33
[58] Field of Search ............................... 435/320.1, 455, 435/6; 536/22.1, 23.1, 24.33

[56] References Cited

U.S. PATENT DOCUMENTS 5,612,458  3/1997  Hyldig-Nielsen et al. ......... 530/388.21

OTHER PUBLICATIONS

Adam, et al., "Nuclear Protein Import in Permeabilized Mammalian Cells Requires Soluble Cytoplasmic Factors", J. Cell Bio. 111:807–816 (1990).

Almarsson, et al., "Peptide nucleic acid (PNA) conformation and polymorphism in PNA–DNA and PNA–RNA hybrids", Proc. Natl. Acad. Sci. USA 90:9542–9546 (1993).

Basu, et al., "Synthesis and Characterization of a Peptide Acid Conjugated to a $_D$–Peptide Analog of Insulin–like Growth Factor 1 for increased Cellular Uptake", Bioconjugate Chem. 8:481–488 (1997).

Bentin, et al., "Enhanced Peptide Nucleic Acid Binding to Supercoiled DNA: Possible Implications for DNA "Breathing" Dynamics", Biochemistry 35:8862–8869 (1996).

Cherny et al., "DNA unwinding upon strand–displacement binding of a thymine–substituted polyamide to double–stranded DNA", Proc. Natl. Acad. Sci. USA 90:1667–1670 (1993).

Demidov, et al., "Sequence selective double strand DNA cleavage by Peptide Nucleic Acid (PNA) targeting using nuclease S1", Nucleic Acids Research 21(9):2103–2107 (1993).

Demidov, et al., "Stability of peptide nucleic acids in human serum and cellular extracts", Biochemical Pharmacology 48(6):1310–1313 (1994).

Demidov, et al., "Kinetics and mechanism of polyamide ("peptide") nucleic acid binding to duplex DNA", Proc. Natl. Acad. Sci. USA (1995).

Dignam, et al., "Accurate transcription initiation by RNA polymearse II in a soluble extract from isolated mammalian nuclei", Nucleic Acids Research 11(5):1475–1489 (1983).

Doh, et al., "Spatial–temporal patterns of gene expression in mouse skeletal muscle after injection of lacZ plasmid DNA", Gene Therapy 4:648–663 (1997).

Dueholm, et al., "Chemistry, properties and applications of PNA (Peptide Nucleic Acid)", New J. Chem. 21:19–31 (1997).

Egholm, et al., "PNA hybridizes to complementary oligonucleotides obeying the Watson–Crick hydrogen–bonding rules", Nature 365:566–568 (1993).

Egholm, et al., "Efficient pH–independent sequence–specific DNA binding by pseudoisocytosine–containing bis–PNA", Nucleic Acids Research 23(2):217–222 (1995).

Felgner, et al., "Enhanced Gene Delivery and Mechanism Studies with a Novel Series of Cationic Lipid Formulations", J. Biol. Chem. 269(4):2550–2561 (1994).

Felgner, et al., "Nomenclature for Synthetic Gene Delivery Systems", Human Gene Therapy 8:511–512 (1997).

Gossen, et al., "Tight control of gene expression in mammalian cells by tetracycline–responsive promoters", Proc. Natl. Acad. Sci. USA 89:5547–555 (1992).

Hanvey, et al., "Antisense and Antigene Properties of Peptide Nucleic Acids", Science 258:1481–1485 (1992).

Hartikka, et al., "An Improved Plasmid DNA Expression Vector for Direct Injection into Skeletal Muscle", Human Gene Therapy 7:1205–1217 (1996).

Hirschman, et al., "Peptide Nucleic Acids Stimulate Gamma Interferon and Inhibit the Replication of the Human Immunodeficiency Virus", J. Investigative Medicine 44(6):347–351 (1996).

Liang, et al., "Novel, high expressing and antibiotic–controlled plasmid vectors designed for use in gene therapy", Gene Therapy 3:350–356 (1996).

Mergny, et al., "Fluorescence Energy Transfer between Two Triple Helix–Forming Oligonucleotides Bound to Duplex DNA", Biochemistry 33:15321–15328 (1994).

Mollegaard, et al., "Peptide nucleic acid DNA strand displacement loops as artificial transcription promoters", Proc. Natl. Acad. Sci. USA 91:3892–3895 (1994).

Nielsen, et al., "Sequence–Selective Recognition of DNA by Strand Displacement with a Thymine–Substituted Polyamide", Science 254:1497–1500 (1991).

Nielsen, et al., "Sequence specific inhibition of DNA restriction enzyme cleavage by PNA", Nucleic Acids Research 21(2):197–200 (1993).

(List continued on next page.)

*Primary Examiner*—Robert A. Schwartzman
*Attorney, Agent, or Firm*—Knobbe, Martens, Olson & Bear LLP

[57] ABSTRACT

Complexes comprising a nucleic acid molecule and a conjugated peptide nucleic acid (PNA). The PNA may be labeled or conjugated to a protein, peptide, carbohydrate moiety or receptor ligand. These complexes are used to transfect cells to monitoring plasmid biodistribution, promote nuclear localization, induce transcriptional activation, lyse the endosomal compartment and facilitate transfection. These complexes increase the efficiency of expression of a particular gene.

27 Claims, 8 Drawing Sheets

OTHER PUBLICATIONS

Nielsen, et al., "Sequence–specific transcription arrest by peptide nucleic acid bound to the DNA template strand", Gene 149:139–145 (1994).

Norton, et al., "Inhibition of human telomerase activity by peptide nucleic acids", Nature Biotechnology 14:615–619 (1996).

Pardridge, et al., "Vector–mediated delivery of a polyamide ("peptide") nucleic acid analogue through the blood–brain barrier in vivo", Proc. Natl. Acad. Sci. USA 92:5592–5596 (1995).

Parente, et al., "Association of a pH–Sensitive Peptide with Membrane Vesicles: Role of Amino Acid Sequence", Biochemistry 29:8713–8719 (1990).

Sixou, et al., "Intracellular oligonucleotide hybridization detected by fluorescence resonance energy transfer (FRET)", Nucleic Acids Research 22(4):662–668 (1994).

Suzuki, et al., "CD4 and CD7 Molecules as Targets for Drug Delivery from Antibody Bearing Liposomes", Exp. Cell Research 193:112–119 (1991).

Szoka, Jr., et al., "Procedure for preparation of liposomes with large internal aqueous space and high capture by reverse–phase evaporation", Proc. Natl. Acad. Sci. USA 75(9):4194–4198 (1978).

Wheeler, et al., "A novel cationic lipid greatly enhances plasmid DNA delivery and expression in mouse lung", Proc. Natl. Acad. Sci. USA 93:11454–11459 (1996).

Wyman, et al., "Design, Synthesis, and Characterization of a Cationic Peptide That Binds to Nucleic Acids and Permeabilizes Bilayers", Biochemistry 36:3008–3017 (1997).

Zelphati, et al., "Mechanism of oligonucleotide release from cationic liposomes", Proc. Natl. Acad. Sci. USA 93:11493–11498 (1996).

SEQUENCE LISTING

<160> NUMBER OF SEQ ID NOS: 7

<210> SEQ ID NO 1
<211> LENGTH: 8
<212> TYPE: DNA
<213> ORGANISM: Artificial Sequence
<220> FEATURE:
<223> OTHER INFORMATION: Primer

<400> SEQUENCE: 1 gagagaga                                                            8

<210> SEQ ID NO 2
<211> LENGTH: 52
<212> TYPE: DNA
<213> ORGANISM: Artificial Sequence
<220> FEATURE:
<223> OTHER INFORMATION: Primer

<400> SEQUENCE: 2
ggtacctctc tctctctctc tctctctctc tctctctctc tctctcggta cc          52

<210> SEQ ID NO 3
<211> LENGTH: 17
<212> TYPE: DNA
<213> ORGANISM: Artificial Sequence
<220> FEATURE:
<221> NAME/KEY: modified_base
<222> LOCATION: (9)...(9)
<223> OTHER INFORMATION: N = pseudoisocytosine
<221> NAME/KEY: modified_base
<222> LOCATION: (11)...(11)
<223> OTHER INFORMATION: N = pseudoisocytosine
<221> NAME/KEY: modified_base

```
<222> LOCATION: (14)...(14)
<223> OTHER INFORMATION: N = pseudoisocytosine
<221> NAME/KEY: modified_base
<222> LOCATION: (16)...(16)
<223> OTHER INFORMATION: N = pseudoisocytosine
<223> OTHER INFORMATION: Primer

<400> SEQUENCE: 3
tctctctcnt nttntnt                                               17

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ccccttggta gagagagaga                                            20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggatccgcaa atgggcggta                                            20

<210> SEQ ID NO 6
<211> LENGTH: 17
<212> TYPE: DNA
<213> ORGANISM: Artificial Sequence
<220> FEATURE:
<223> OTHER INFORMATION: Primer

<400> SEQUENCE: 6
cggccgcgca ggctgga                                               17

<210> SEQ ID NO 7
<211> LENGTH: 57
<212> TYPE: DNA
<213> ORGANISM: Artificial Sequence
<220> FEATURE:
<223> OTHER INFORMATION: Primer

<400> SEQUENCE: 7
atctctctct ctctctctct ctctctctct ctctctctct ctctctctcg gatccag    57
```

CHEMICAL MODIFICATION OF DNA USING PEPTIDE NUCLEIC ACID CONJUGATES

RELATED APPLICATIONS

This application is a continuation of application Ser. No. 09/087,815, filed May 29, 1998 (abandoned), which claims priority under 35 U.S.C. §119(e) to Provisional Application Serial No. 60/059,215, filed Sep. 18, 1997.

FIELD OF THE INVENTION

The present invention relates to peptide nucleic acid (PNA) conjugates and a method for binding these conjugates to DNA for diagnostic and therapeutic applications. More particularly, the invention relates to PNA linked to fluorophores or peptides which hybridize to DNA and can be used to monitor the intracelliuar location of exogenous transfected DNA and to promote various intracellular processes.

BACKGROUNDS OF THE INVENTION

Plasmid based, non-viral gene delivery systems have been shown to be promising for the treatment of major inherited and acquired diseases, and for the development of a new approach to vaccination (Wolff et al., *Science* 247:1465–1468, 1990; Ulmer et al., *Science* 259:1745–1749,1993; Donnelly et al., *Life Sci.* 60:163–172, 1997; Gao et al., *Gene Ther.* 2:710–722, 1995; Felgner, *Ann. N.Y. Acad. Sci.* 772:126–139, 1995). Although the numbers of human gene therapy trials with these technologies are increasing, their efficiencies and clinical potencies are currently limited due to low levels of in vivo gene product expression (Felgner, *Hum. Gene Ther.* 7:1791–1793, 1996). Commonly used approaches for increasing in vivo expression include improving the DNA delivery system (Gao et al., *Gene Therapy* 2:710–722, 1995; Felgner, supra.; Behr, *Bioconj. Chem.* 5:382–389, 1994) or optimizing the DNA sequence at the level of the promoter, enhancer, intron or terminator (Hartikka et al., *Hum. Gene Ther.* 7:1205–1217, 1996; Liang et al., *Gene Therapy* 3:350–356, 1996).

In conventional small molecule drug development, it is common to make systematic chemical modifications of the biologically active agent itself in order to improve its bioavailability and efficacy. This research and development activity is referred to as medicinal chemistry. The ability to carry out a medicinal cherrmstry approach to improve the bioavailability of DNA is presently lacking because the methods that have been employed to directly modify DNA either reduce or destroy its ability to be transcribed. In addition, the available approaches to chemically modify plasmids which involve photolysis, nick translation, or the use of chemically active nucleotide analogs, randomly attack the DNA so that the final product is chemically heterogeneous and poorly defined.

Several methodologies, including electron microscopy, fluorescence in situ hybridization (FISH), in situ polymerase chain reaction (PCR), DNA intercalating dyes and radio-, biotin-, gold-, or fluorescent-labeled DNA, have been used to follow the delivery of DNA in cells (Loyter et al., *Proc. Natl. Acad. Sci. U.S.A.* 79:422–426, 1982; Tsuchiya et al. *J. Bacteriol.* 170:547–551, 1988; Chowdhury, 1993; Zabner et al., *J. Biol. Chem.* 270:18997–19007, 1995; Dowty et al., *Proc. Natl. Acad. Sci. U.S.A.* 92:4572–4576, 1995; Bordignon et al., *Science* 270:470–475, 1995; Dean, *Exp. Cell Res.* 230:293–302, 1997). However, these methods have practical and technical limitations, which can lead to difficulties in interpretation. Electron microscopy, FISH and in situ PCR require cell fixation, lysis, and lengthy manipulations, and these procedures have been shown to influence the detection sensitivity and pattern of DNA distribution in cells. DNA intercalating fluorescent dyes, bind weakly to plasmid and exchange with endogenous nucleic acid raising questions about the intracellular source of the fluorescent signal. Other covalent fluorescent labeling methods which utilize nick translation or photoaffinity labeling result in chemical breakdown of the starting material, and thus any observations made with these materials may not be representative of the behavior of the original intact plasmid. None of the technologies presented above allow direct detection of structurally and finctionally intact plasmid in a real-time fashion in viable cells.

Peptide nucleic acids (PNA) have been developed to hybridize to single and double stranded nucleic acids. PNA are nucleic acid analogs in which the entire deoxyribose-phosphate backbone has been exchanged with a chemically completely different, but structurally homologous, polyamide (peptide) backbone containing 2-aminoethyl glycine units. Unlike DNA, which is highly negatively charged, the PNA backbone is neutral. Therefore, there is much less repulsive energy between complementary strands in a PNA-DNA hybrid than in the comparable DNA-DNA hybrid, and consequently they are much more stable. PNA can hybridize to DNA in either a Watson/Crick or Hoogsteen fashion (Demidov et al., *Proc. Natl. Acad. Sci. U.S.A.* 92:2637–2641, 1995; Egholm, *Nature* 365:566–568, 1993; Nielsen et al., *Science* 254:1497–1500, 1991; Dueholm et al., *New J. Chem.* 21:19–31, 1997).

Molecules called PNA "clamps" have been synthesized which have two identical PNA sequences joined by a flexible hairpin linker containing three 8-amino-3,6-dioxaoctanoic acid units. When a PNA clamp is mixed with a complementary homopurine or homopyrimidine DNA target sequence, a PNA-DNA-PNA triplex hybrid can form which has been shown to be extremely stable (Bentin et al., *Biochemistry* 35:8863–8869, 1996; Egholm et al., *Nucleic Acids Res.* 23:217–222, 1995; Griffith et al., *J. Am. Chem. Soc.* 117:831–832, 1995).

The sequence-specific and high affinity duplex and triplex binding of PNA have been extensively described (Nielsen et al., *Science* 254:1497–1500, 1991; Egholm et al., *J. Am. Chem. Soc.* 114:9677–9678, 1992; Egholm et al., *Nature* 365:566–568, 1993; Almarsson et al., *Proc. Natl. Acad. Sci. U.S.A.* 90:9542–9546, 1993; Demidov et al., *Proc. Natl. Acad. Sci. U.S.A.* 92:2637–2641, 1995). They have also been shown to be resistant to nuclease and protease digestion (Demidov et al., *Biochem. Pharm.* 48:1010–1313, 1994). PNA has been used to inhibit gene expression (Hanvey et al., *Science* 258:1481–1485,1992; Nielsen et al., *Nucl. Acids. Res.*, 21:197–200, 1993; Nielsen et al., *Gene* 149:139–145, 1994), to block restriction enzyme activity (Nielsen et al., supra., 1993), to act as an artificial transcription promoter (Mollegaard, *Proc. Natl. Acad. Sci. U.S.A.* 91:3892–3895, 1994) and as a pseudo restriction endonuclease (Demidov et al., *Nucl. Acids. Res.* 21:2103–2107, 1993). Recently, PNA has also been shown to have antiviral and antitumoral activity mediated through an antisense mechanism (Norton, *Nature Biotechnol.*, 14:615–619, 1996; Hirschman et al., *J. Investig. Med.* 44:347–351, 1996). PNAs have been linked to various peptides in order to promote PNA entry into cells (Basu et al., *Bioconj. Chem.* 8:481–488, 1.997; Pardridge et al., *Proc. Natl. Acad Sci. U.S.A.* 92:5592–5596, 1995). However, hybridization of PNA-peptide complexes to DNA, and transfection of cells with these complexes, has not been reported. In addition, the use of PNA-peptide conjugates for improving the bioavailability of plasmid DNA and for increasing transgene expression has not been previously described.

The ideal probe for irreversible chemical modification of plasmid will not damage the plasmid, and thus will not interfere with its transcription or intracellular trafficking. The plasmid structure, biological activity and stability would be the same with or without probe. The probe should be sequence-specific in order to differentiate delivered plasmid from endogenous nucleic acid and the probe itself should not have any influence on plasmid function. All of the technologies discussed above for chemically modifying plasmid DNA result in DNA damage and interfere with its transcriptional activity. Further, none of the technologies mentioned above allow direct detection of structurally and functionally intact plasmid in a real-time fashiion on viable cells. The present invention provides a straightforward and versatile approach to permanently introduce new physical and biological properties into DNA by irreversible plasmid modification.

SUMMARY OF THE INVENTION

One embodiment of the present invention is a composition comprising a nucleic acid molecule and a conjugated peptide nucleic acid (PNA) molecule associated with said DNA molecule, wherein the PNA molecule contains a region complementary to the DNA molecule. In one aspect of this preferred embodiment, the nucleic acid molecule is DNA or RNA. Advantageously, the DNA is linear double stranded DNA, linear single stranded DNA, circular double stranded DNA or circular single stranded DNA. Preferably, the DNA molecule is a plasmid. In another aspect of this preferred embodiment, the plasmid encodes a reporter gene. Alternatively, the plasmid encodes a therapeutic gene. Advantageously, the reporter gene is β-galactosidase, luciferase, chloramphenicol acetyltransferase green fluorescence protein or secreted alkaline phosphatase. Preferably, the PNA is conjugated to a fluorescent, colorimetric, radioactive or enzymatic label. In another aspect of this preferred embodiment, the PNA is conjugated to a protein, peptide, carbohydrate moiety or receptor ligand. Preferably, the peptide is a nuclear localization signal peptide, endosomal lytic peptide, transcriptional activator domain peptide, receptor specific peptide or immunostimulatory peptide.

The present invention also provides a method for determining the biodistribution of exogenous transfected nucleic acid molecule in a cell, comprising the steps of: contacting the exogenous nucleic acid molecule with a conjugated IINA in a sequence-specific manner prior to transfection; transfecting the cell with the labeled PNA; and monitoring the intracellular location of the nucleic acid molecule. In one aspect of this preferred embodiment, the nucleic acid molecule is DNA or RNA. Advantageously, the DNA is linear double stranded DNA, linear single stranded DNA, circular double stranded DNA or circular single stranded DNA. Preferably, the DNA is a plasmid. Advantageously, the PNA is conjugated to a fluorescent, calorimetric, radioactive or enzymatic label. In another aspect of this preferred embodiment, the transfecting step is mediated by cationic lipids.

Still another embodiment of the present invention is a method for enhancing the delivery of exogenous transfected nucleic acid molecule into the nuclear compartment of a cell, comprising the step of hybridizing the exogenous nucleic acid molecule to a PNA conjugated to a nuclear localization signal peptide prior to transfection. In one aspect of this preferred embodiment, the nucleic acid molecule is DNA or RNA. Advantageously, the DNA is linear double stranded DNA, linear single stranded DNA, circular double stranded DNA or circular single stranded DNA. Preferably, the DNA is plasmid DNA. Advantageously, the transfection is mediated by cationic lipids. In another aspect of this preferred embodiment, the nuclear localization signal peptide is poly-L-lysine, SV40 NLS, antennapedia peptide, TAT peptide, c-myc peptide, VirD2 peptide, nucleoplasmin peptide, ARNT derived peptide or M9 domain peptide.

The present invention also provides a method for promoting transcription of exogenous transfected DNA in a cell, comprising the step of hybridizing the exogenous DNA to a PNA conjugated to a transcription activator domain peptide prior to transfection. Advantageously, the exogenous transfected DNA is linear double stranded DNA, linear single stranded DNA, circular double stranded DNA or circular single stranded DNA. Preferably, the exogenous transfected DNA is plasmid DNA. Advantageously, the transfection is mediated by cationic lipids. In one aspect of this preferred embodiment, the transcription activator domain peptide is VP16 (337–347)2, P65 (520–550), Oct-2 (143–160), Sp1 (340–385), random acidic sequences or ERM (33–52).

Yet another embodiment of the present invention is a method for preventing entrapment of exogenous transfected nucleic acid molecule in the endosomal compartment of a cell, comprising the step of hybridizing the exogenous nucleic acid molecule to a PNA conjugated to an endosomal lytic peptide prior to transfection. In one aspect of this preferred embodiment, the nucleic acid molecule is DNA or RNA. Advantageously, the DNA is linear double stranded DNA, linear single stranded DNA, circular double stranded DNA or circular single stranded DNA. Preferably, the DNA is plasmid DNA. Advantageously, the transfection is mediated by cationic lipids. In another aspect of this preferred embodiment, the endosomal lytic peptide is HA derived peptide, GALA, KALA, EALA, melittin-derived peptide, a-helical peptide or Alzheimer β-amyloid peptide.

The present invention also provides a method for increasing the transfection efficiency of a transfected nucleic acid molecule in a cell, comprising the step of hybridizing the exogenous nucleic acid molecule to a PNA conjugated to a receptor specific ligand prior to transfection. In one aspect of this preferred embodiment, the nucleic acid is DNA or RNA. Advantageously, the DNA is linear double stranded DNA, linear single stranded DNA, circular double stranded DNA or circular single stranded DNA. Preferably, the DNA is plasmid DNA. Advantageously, the transfection is mediated by cationic lipids. In another aspect of this preferred embodiment, the receptor specific ligand is a sugar, immunoglobulin, IGF-1 derived peptide, αV-integrin, epidermal growth factor, asialoglycoprotein, folate, transferrin or α2-macroglobulin.

Another embodiment of the invention is a method for screening compounds which activate transcription, comprising the steps of: linking a compound to a PNA; hybridizing a plasmid encoding a reporter gene to the PNA containing said linked compound; transfecting a cell with the plasmid-PNA-compound complex; determining the level of expression of the reporter gene; and comparing the level of expression of the reporter gene to the level of expression of the reporter gene in a cell transfected with the plasmid-PNA complex, wherein an increase in reporter gene expression in the presence of the compound indicates that the compound is an activator of transcription. Preferably, the reporter gene is β-galactosidase, luciferase, chloramphenicol acetyltransferase green fluorescence protein or secreted alkaline phosphatase.

The present invention also provides a method for screening compounds which promote cellular uptake of an exogenous nucleic acid molecule, comprising the steps of linking a compound to a PNA; hybridizing a nucleic acid molecule to the PNA containing the linked compound; transfecting a cell with the nucleic acid-PNA-compound complex; determining the intracellular amount of the nucleic acid molecule; and comparing the intracellular level of the nucleic acid molecule to a cell transfected with a control complex not containing the compound, wherein an increase in the amount of the nucleic acid molecule in the cell compared to the control cell indicates that the compound promotes cellular uptake of the exogenous nucleic acid molecule. In one aspect of this preferred embodiment, the nucleic acid molecule is DNA or RNA. Advantageously, the DNA is linear double stranded DNA, linear single stranded DNA, circular double stranded DNA or circular single stranded DNA. Preferably, the DNA is plasmid DNA.

Another embodiment of the present invention is a kit, comprising: a plasmid comprising a PNA binding site and a multiple cloning site for insertion of a nucleic acid sequence; a labeled PNA capable of binding to the PNA binding site; and sequencing primers complementary to the multiple cloning site. The kit may further comprise a labeling buffer. Preferably, the PNA is fluorescently labeled. Alternatively, the PNA is labeled with a chemical group capable of reacting with a chemical group on a protein. Preferably, the chemical group is pyridyldithiol or maleimide.

The present invention also provides a method for enhancing the immunogenicity of a protein or peptide encoded by an exogenous transfected DNA molecule, comprising the step of hybridizing the exogenous DNA molecule to a PNA conjugated to an immunostimulatory molecule prior to transfection. Preferably, the imnhunostimulatory molecule is a lymphokine, cytokine, muramyl dipeptide, complement-derived peptide or oligonucleotide. Advantageously, the oligonucleotide is a CpG dinucleotide repeat. Advantageously, the exogenous transfected DNA molecule is linear double stranded DNA, linear single stranded DNA, circular double stranded DNA or circular single stranded DNA. Preferably, the DNA is plasmid DNA.

DETAILED DESCRIPTION OF THE PREFERRED EMBODIMENTS

The present invention provides a method for permanently introducing new physical and biological properties into a nucleic acid molecule by irreversible chemical modification using PNA probes. These properties include increased transfection efficiency, nuclear localization, transcription activation, endosomal lytic activity and immunostimulatory activity. The PNA probe can be conjugated to a fluorescent label, radioactive label, calorimetric label, enzymatic label, protein, peptide, ligand, other carbohydrate moiety or other small molecule. In fact, the conjugation of any desired molecule capable of facilitating the delivery of a nucleic acid molecule, and the expression of gene product encoded by the nucleic acid molecule, to a PNA is within the scope of the invention. Assays for determining the ability of a molecule to facilitate these events are disclosed in the examples presented hereinbelow. PNA can also be conjugated to a fluorescent, enzymatic, radioactive or colorimetric label to allow monitoring of plasmid bioavailability, intracellular localization and expression of the encoded gene.

The PNA probe does not disturb the conformation (gel mobility), nuclease sensitivity or transcriptional activity of the DNA to which it hybridizes. The PNA or PNA clamp hybridizes to duplex DNA in a very high affinity and sequence-specific manner, and are nuclease and protease resistant. The PNA conjugates improve the delivery and expression of DNA both in vitro and in vivo.

Figure 1:
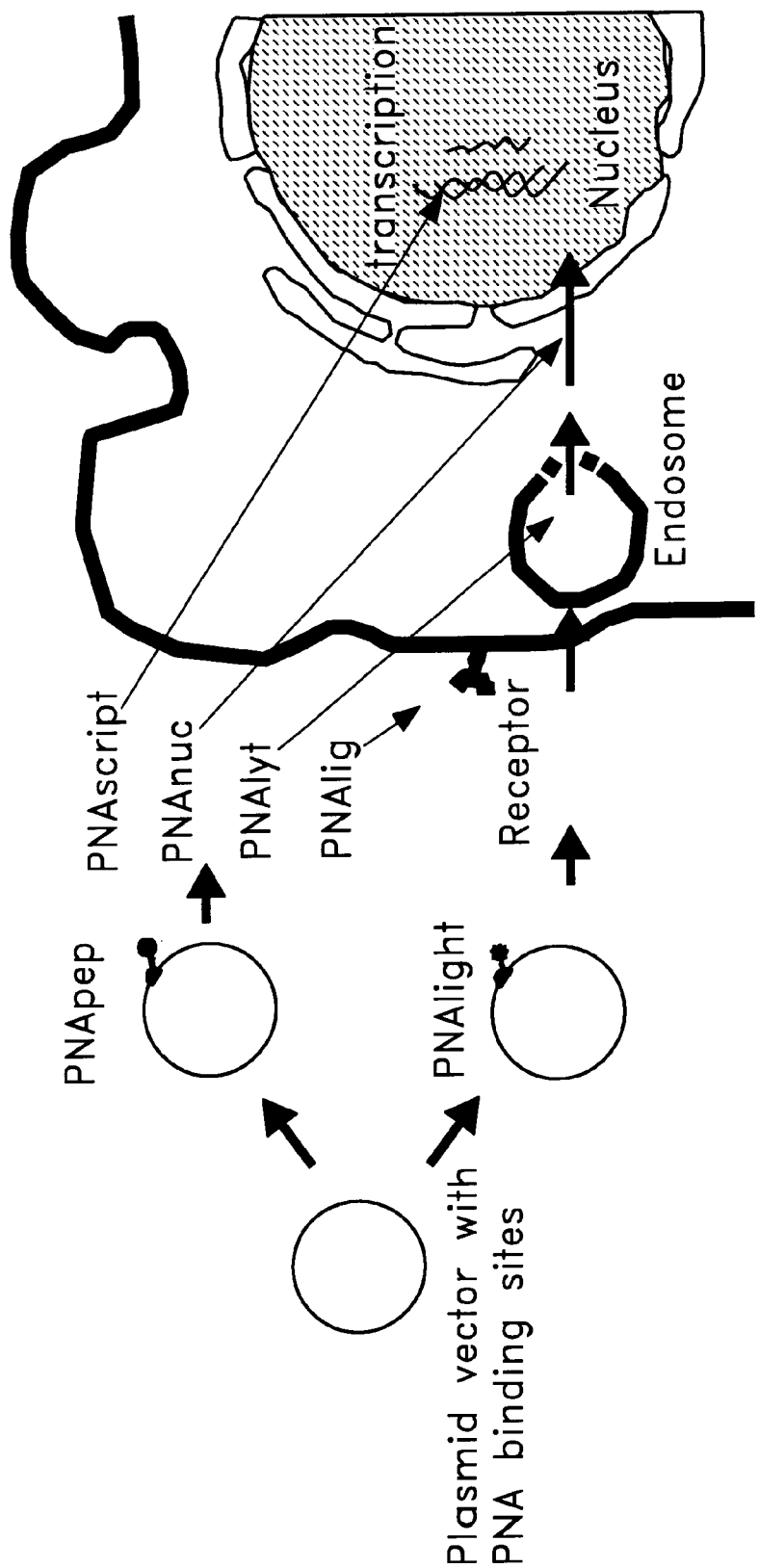
FIG. 1 is a schematic diagram showing cellular applications of plasmids hybridized to a PNA-peptide complex. PNApep=plasmid with a peptide bound via a PNA clamp; PNAnuc=plasmid with a nuclear localization signal peptide; PNAlyt=plasmid with a endosomolytic or fusogenic peptide; PNAlig=plasmid with a receptor specific ligand; PNAlight=plasmid with a bound fluorophore.

PNA dependent gene chemistry technology is used to conjugate biologically active molecules including peptides, proteins and carbohydrate moieties onto nucleic acid molecules including linear single stranded DNA, circular single stranded DNA, linear double stranded DNA, circular double stranded DNA and RNA. In a preferred embodiment, these biologically active molecules are coupled to a plasmid. Irreversible peptidic modifications of transcriptionally active plasmids have several applications which are illustrated schematically in FIG. 1. The addition of a nuclear localization peptide onto a nucleic acid molecule facilitates its uptake into the nucleus of transfected cells. Nuclear localization signals are peptides from 5 to about 20 amino acids that can facilitate nuclear uptake of large macromolecules such as protein, RNA, single stranded DNA and even micron sized gold beads. In these cases, uptake is rapid, occurring within minutes, and does not require cell division. A nuclear localization signal coupled to a plasmid that is effective at delivering the plasmid across the intact nuclear membrane of transfected cells would be expected to yield higher levels of transgene expression at lower plasmid levels. Nuclear localization signal facilitated plasmid delivery should not require cell division, and the time to onset of expression should be shorter if cell division is not required.

Nuclear localization peptides contemplated for use in the present invention include, but are not limited to, poly-L-lysine (Blanke et al., *Proc. Natl. Acad. Sci. U.S.A.*, 93:8437–8442, 1996; Wadhwa et al., *Bioconj. Chem.* 8:81–88, 1997), SV40 NLS (Dingwall et al., *Trends Biochem. Sci.* 16:478–481, 1991; Lanford et al., *Cell* 46:575–582, 1986), antennapedia peptide (Derossi et al., *J. Biol. Chem.* 269:10444–10450, 1994; Derossi, *Restor. Neurol. Neurosci.* 8:17–18, 1995), TAT peptide (Fawell et al., *Proc. Natl. Acad. Sci. U.S.A.* 91:664–668, 1994; Vives et al. *J. Biol. Chem.*, 272:16010–16017, 1997), c-myc peptide (Dang et al., *Mol. Cell. Biol.* 8:4048–4054, 1988; Nigg, *Nature* 386:779–787, 1997), VirD2 peptide (Howard et al., *Cell* 68:109–118, 1992; Ballas et al., *Proc. Natl. Acad. Sci. U.S.A.* 94:10723–10728, 1997), nucleoplasmin peptide (Nigg et al., supra.; Burglin et al., *EMBO J.* 6:2617–2625, 1987), ARNT derived peptide (Eguchi et al., *J. Biol. Chem.* 272:17640–17647, 1997) and M9 domain peptide (Pollard et al., *Cell* 86:985–994, 1996). Nuclear localization peptides can be used to target a plasmid encoding a transcription factor which activate expression of a particular gene.

Most of the available synthetic gene delivery systems are endocytosed by cells and the delivery system with its entrapped DNA ends up in the endoso,mal compartment. If the DNA or its delivery system lacks a mechanism to break out of the endosomal compartment, it will be delivered to the lysosome and degraded. Effective gene delivery systems, therefore, usually have a built in system for endosomal escape. A variety of endosomal lytic peptides have been shown to be effective at contributing an endosomal escape function into synthetic gene delivery systems (Wyman et al., supra.; Wagner et al., *Proc. Natl. Acad. Sci. U.S.A.* 89:7934–7938, 1992; Kichler, *Bioconj. Chem.* 8:213–221, 1997; Plank et al., *J. Biol. Chem.* 269:12918–12924, 1994; Haensler et al., *Bioconj. Chem.* 4:372–379, 1993). In all of these examples, the endosomal lytic peptide is incorporated into the delivery system and not directly on the DNA. Attaching endosomal lytic peptides directly onto the DNA enables the plasmid to be more efficiently released from the endosomal compartment. Endosomal lytic peptides contemplated for use in the present invention include, but are not limited to, HA derived peptide (Wagner et al., supra; Plank et al., supra.), GALA (Subbatao et al., *J. Biol. Chem.* 26:2964–2972, 1987; Parente et al., supra.), KALA (Wyman et al., supra.), EALA (Vogel et al. (*J. Am. Chem. Soc.* 118:1581–1586, 1996), melittin-derived peptide (Kichler et al., supra.), α-helical peptide (Niidome et al., *J. Biol. Chem.* 272:15307–15312, 1997) and Alzheimer β-amyloid peptide (Pillot et al., *J. Biol. Chem.* 271:28757–28765, 1996).

The addition of a ligand that can bind to a cell surface receptor may lead to more efficient uptake into cells or result in specific uptake into a subpopulation of cells. Naked plasmid DNA can be taken up and expressed by cells in vivo and some reports suggest that the DNA in this system is taken up by a specific, receptor dependent mechanism (Wolff et al., *Science* 247:1465–1468, 1990; Ulmer et al., *Science* 259:1745–1749, 1993; Meyer et al., *Gene Therapy* 2:450–460, 1995). In some cases, the efficiency of synthetic gene delivery systems has been shown to be greatly enhanced by incorporating specific ligands for cell surface receptors into the carrier. Attachment of specific ligands directly onto the plasmid may lead to more efficient in vivo uptake and expression of naked DNA, as well as DNA that is delivered in a carrier. Specific ligands contemplated for direct attachment to a plasmid include, but are not limited to, mannose, galactose, immunoglobulins, IGF-1 derived peptide, αV integrins (RGD motif), EGF, asialoglycoprotein, folate, transferrin and α2-microglobulin.

PNA can also carry artificial transcription activation domains which represent intrinsically transcriptionally potent vectors for improved gene therapy systems. These activation domains are linked to PNA using the method described in Example 12. The PNA-peptide conjugate is then hybridized to a plasmid containing a desired gene. Typical expression plasmids contain a promoter, an enhancer, a coding sequence and a terminator. The promoter region of the plasmid binds RNA polymerase II, associated enzymes and other factors, which are required to initiate transcription (Mitchell et al., *Science* 245:371–378, 1989). Plasmids containing the promoter region, but lacking enhancer sequences, usually fail to efficiently transcribe the message. The function of enhancer sequences is to bind specific intracellular transcription factors. The DNA-bound transcription factors interact with the transcription complex and increased the transcription rate. Normal endogenous transcription factors are proteins that contain two domains, the DNA binding domain and the transcription activation domain (Brent et al., *Cell* 43:729–736, 1985). The DNA binding domain binds to specific duplex DNA sequences, usually 5–10 base pairs, located in the enhancer region. The DNA binding domain brings the transcription activation domain into proximity of the minimal promoter where it interacts with RNA polymerase to activate transcription.

Transcription factor mediated activation has been elucidated, in part, by studies using fusion proteins comprising various combinations of DNA binding domains and different transcription activation domains. By cloning different sequences into the transcription activation domain of these chimeric proteins, sequences capable of activating transcription were identified. Three major classes of transcription activation domains have been identified: proline-rich, glutamine-rich and acidic (Mitchell et al., supra.; Courey et al., *Cell* 55:887–898, 1988; Tanaka et al., *Mol. Cell. Biol* 14:6046–6055, 1994; Ma et al., *Cell* 51:113–119, 1987). The shortest sequences that can confer transcription activation are the acidic domains (Seipel et al., *EMBO J.* 11:4961–4968, 1992). Transcription activation domain peptides contemplated for use in the present invention include, but are not limited to, VP16 (337–347)2 (Seipel et al., supra.), P65 (520–550) (Pettersson et al. (*J. Mol Biol.* 214:373–380, 1990), Oct-2 (143–160) (Seipel et al., supra.; Tanaka et al., supra.), Sp1 (340–385) (Seipel et al., supra.), random acidic sequences (Ma et al., *Cell* 51:113–119, 1987) and ERM (33–52) (Defossez et al., *Nucleic Acids. Res.* 25:4455–4463, 1997). The use of peptidometics and proteins is also contemplated.

Immunostimulatory agents may also be conjugated to PNA and used to increase immune system function. These agents include peptides such as lymphokines, cytokines, muramyl dipeptide and complement-derived peptides. In addition, CpG dinucleotide repeats, which are known to have immunostimulitory effects, can be conjugated to PNA. The use of other oligonucleotides which also have immunostimulatory effects is also within the scope of the present invention.

In another preferred embodiment of the invention, random peptide libraries or libraries of other compounds (e.g., small organic molecules, peptidomimetics) are screened using high throughput screening assays to discover transcriptional activators. Peptide, nucleic acid and polysaccharide-based compounds may be synthesized by random and directed synthesis (Lam et al., *Nature* 354:82–86, 1991). Alternatively, libraries of natural compounds in the form of bacterial, fungal, plant and animal extracts are available or readily producible. Additionally, natural and synthetically produced libraries and compounds are readily modified through conventional chermical, physical and biochemical means. Any desired compound may be screened for potential transcription activation activity.

Compounds are coupled to PNA using standard methods. For example, peptides are linked to PNA using crosslinking agents as described in Example 12 and the peptide-PNA conjugate is hybridized to a DNA molecule prior to cell transfei-tion. These peptides improve the efficiency of transfection, promote nuclear DNA localization, promote endosomal lysis or activate transcription as described in more detail below. Labeled PNAs are hybridized to DNA molecules, preferably plasmids, and used to monitor plasmid biodistribution after cell transfection or to monitor expression of a reported gene contained within the plasmid. The use of various labels is contemplated, including radiolabels, colorimetric labels and enzymatic labels (e.g., alkaline phosphatase, horseradish peroxidase) which are well known in the art. Fluorescently labeled PNA are available from commercial sources such as PerSeptive Biosystems, Framingham, Ma. The compound-PNA complex is then hybridized to a plasmid encoding a reporter gene, followed by transfecting a cell with the PNA-compound-plasmid complex, and assaying reporter gene activity compared to a control complex not containing the compound. These methods are described in the examples presented herein. Similar methodology can be used to identify peptides, peptidomimetics and other compounds which promote nucleic acid uptake (transfection efficiency), nuclear localization, endosomal lysis and receptor-mediated PNA uptake using the various assays described in the examples presented herein.

For example, a compound can be screened for its ability to promote the transfection efficiency of an exogenous nucleic acid molecule, preferably a plasmid, by conjugating the compound to a PNA, hybridizing the PNA-plasmid complex to the exogenous nucleic acid molecule and contacting a cell with this complex. The amount of the nucleic acid molecule present in the cell is determined by, for example, agarose gel electrophoresis and ethidium bromide staining. This amount is compared to the amount present in cells transfected with the same complex, in the absence of compound. An increased amount of exogenous nucleic acid molecule in cells transfected in the presence of the compound indicates that the compound stimulates nucleic acid uptake.

Although particular PNA molecules, reporter genes and peptides linked to PNA are exemplified herein, these examples are merely illustrative and the use of any PNA molecule, reporter gene and peptide is within the scope of the invention.

The plasmid may also comprise a therapeutic gene and the PNA conjugation methods described herein may be used to increase transfection efficiency, nuclear localization and expression of a therapeutic gene for gene therapy applications. The plasmid may encode any desired gene product which is absent or present at reduced levels in an organism. Nonlimiting examples of these gene products are the cystic fibrosis transmembrane receptor (CFTR), insulin, dystrophin, interleukin-2, interleukin-12, erythropoietin, gamma interferon and granulocyte macrophage colony stimulating factor.

Peptides are synthesized using a conventional peptide synthesizer, coupled to PNA and the peptide-PNA complex is hybridized to a DNA sequence containing a region complementary to the PNA. The PNA-labeled DNA is then used to transfect cells either in vitro or parenterally administered to a vertebrate, preferably a mammmal, more preferably a human, in vivo.

The chemically modified plasmids discussed hereinabove are useful tools in the design and implementation of synthetic gene delivery systems and improve the efficiency of synthetic gene delivery systems for gene therapy applications. These PNA-labeled plasmids can be used to gain a better understanding of the cellular and molecular barriers to DNA delivery and to develop new insights leading to more effective plasmid delivery systems. Conjugated PNA probes capable of hybridizing to a nucleic acid sequence of interest can be used as chemical reagents to modify plasmid DNA and improved its bioavailability, transfection efficiency, expression, nuclear localization and other beneficial properties.

The present invention also includes a method for effectively monitoring plasmid biodistribution in living cells following transfection using a highly fluorescent preparation of plasmid DNA prepared by hybridizing a fluorescent conjugated PNA triplex clamp to the complementary region of a plasmid or other DNA molecule. Although any transfection method well known in the art may be used, including calcium phosphate precipitation, electroporation and DEAE-dextran, cationic lipidmediated transfection is preferred. Gene delivery systems are described by Felgner et al. (*Hum. Gene Ther.* 8:511–512, 1997) and include cationic lipid-based delivery systems (lipoplex), polycation-based delivery systems (polyplex) and a combination thereof (lipopolyplex). Cationic lipids are described in U.S. Pat. Nos. 4,897,355 and 5,459,127, the entire disclosures of which are hereby incorporated by reference. A fluorescent PNA probe allows quantitative time-dependent tracking of DNA in living cells, and it can be used in association with the green fluorescent protein (GFP) encoded on the same plasmid. GFP has been shown to be a versatile and sensitive reporter gene, allowing rapid and quantitative monitoring of gene expression in realtime by microscopy and by cell sorting (Chalfie et al., *Science* 263:802–805, 1994; Heim et al., *Nature* 373:663–664, 1995; Cheng et al., *Nature Biotechnol.* 14:606–609, 1996).

Entry of exogenous transfected DNA across the nuclear envelope and into the nuclear compartment of non-dividing transfected cells is a very inefficient process in which non-dividing cells exhibit very little, if any, expression of transfected genes. Transfection and expression of exogenous transfected DNA in cells in vivo is significantly more difficult than transfection of cells in vitro due to the presence of a virtually intact nuclear membrane which DNA cannot efficiently traverse. In contrast, in rapidly proliferating cells, the nuclear membrane is constantly broken down and reformed. The cationic lipids used to mediate plasmid DNA transfection cannot themselves dissolve the nuclear membrane.

Figure 2:
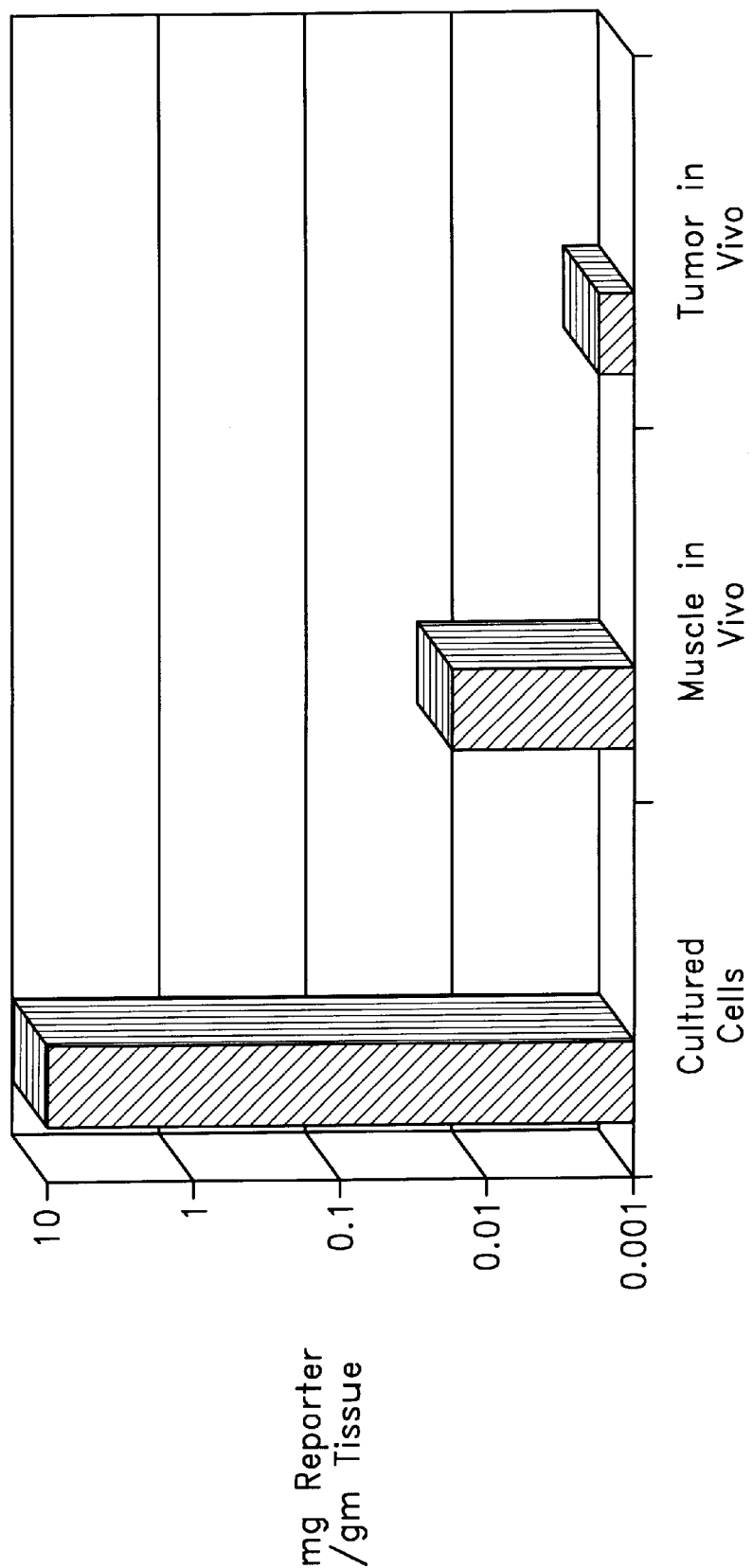
FIG. 2 shows reporter gene expression efficacy in cultured cells, muscle cells and tumor cells.

FIG. 2 compares the level of gene product expression obtainable after in vivo administration of a plasmid encoding a reporter gene with the level that can be obtained in cultured cells. As shown in FIG. 2, the amount of gene product recovered following intramuscular or intratumor plasmid injection is 3–4 orders of magnitude lower than that which can be obtained in cultured cells. Thus, there is room to improve the in vivo non-viral gene delivery system technology before it reaches an efficiency level comparable to in vitro transfection. For gene therapy applications, it is critical for non-dividing cells to take up and express exogenous DNA. For example, for genetic disorders in which a particular protein is lacking or present at very low levels, DNA encoding the protein must cross both the cytoplasmic and nuclear membranes to ensure expression of the encoded protein. Accordingly, it is desirable to specifically associate plasmid or non-plasmid DNA with both PNA and a ligand which facilitates traversal of the nuclear membrane and subsequent expression of the DNA. In a preferred embodiment, moieties which facilitate transport of DNA across the nuclear membrane are attached to the PNA. Such moieties include peptides called nuclear localization signals, proteins and other ligands.

Although the use of PNA triplexes are described herein, other molecules which are capable of triplex formation and hybridization in a sequence-specific manner to DNA are also contemplated such as those described in U.S. Pat. No. 5,460,941, the entire contents of which are hereby incorporated by reference.

Fluorescent plasmids prepared by this method are neither functionally nor conformationally altered. PNA binding is sequence-specific, saturable, extremely stable and does not influence the nucleic acid intracellular distribution in cells. Fluorescent plasmid and green fluorescent protein (GFP) expressed from the same plasmid could be co-localized in cells, and GFP is shown to be expressed only in cells containing detectable nuclear fluorescent plasmid. This method provides a basis to elucidate the mechanism of plasmid delivery and nuclear import using synthetic gene delivery systems.

To determine the biodistribution of transfected DNA, a DNA molecule or plasmid containing a DNA molecule of interest is contacted with a PNA probe having a nucleic acid region complementary to the DNA molecule of interest such that the probe and the DNA molecule form a tightly bound triplex as described in Example 1. The PNA probe also has a label associated therewith, preferably a fluorescent label, to allow real time measurement of DNA movement within the cell by fluorescence-based assays. The PNA/DNA complex is then used to transfect cells either in vitro, in vivo or ex vivo which are monitored using these assays.

To facilitate entry of a DNA molecule of plasmid containing a DNA molecule of interest, the PNA probe is associated with a moiety which facilitates entry of the DNA into the nuclear compartment of the cell. The PNA/DNA complex is then used to transfect cells either in vitro, in vivo or ex vivo. The PNA/DNA complex efficiently enters the nuclear compartment due to the facilitating moiety attached to the PNA probe. For gene therapy applications, the complex is systemically or locally administered to an individual, preferably a human. Alternatively, the PNA/I)NA complex is used to transfect cells taken from an individual ex vivo, then returned to the individual after transfection.

Another embodiment of the invention is a kit which allows placement of a gene of interest into an expression vector and labeling of the expression vector with a peptide or fluorescent tag. Any desired expression vector is within the scope of the invention, including plasmid vectors, retroviral vectors and adenoviral vectors, although plasmid vectors are preferred. The kit contains a labeled PNA and a plasmid which has a multiple cloning site (MCS) and a region complementary to PNA to allow PNA binding. The kit also contains sequencing primers to allow sequencing of the gene of interest to confirm that the correct sequence was inserted into the multiple cloning site of the expression vector. The kit may also comprise labeling and reaction buffers. The PNA contains a fluorescent tag, a colorimetric label, a radiolabel or a chemical group capable of reacting with chemical groups found on proteins.

A variety of crosslinking agents can be used to target different chemical groups on proteins, including amino, carboxyl, sulfhydryl, aryl, hydroxyl and carbohydrates. Many of these crosslinking reagents are available from Pierce Chemical Co. (Rockford, Ill.) and described in the Pierce catalog. Heterodifinctional crosslinkers contain two or more different reactive groups that allow for sequential conjugations with specific groups of proteins, minimizing undesirable polymerization or selfconjugation. Heterodifiuctional crosslinkers which react with primary or secondary amines include imidoesters and N-hydroxysuccinimide (NHS)-esters such as succimidyl 4-(N-maleimidomethyl) cyclohexane-1 -carboxylate (SMCC) and succimidyl-4-(p-maleimidophenyl)-butyrate (SMPB). Cross-linkers which react with sulfhydryl groups include maleimides, haloacetyls and pyridyl disulfides Carbodiimide cross-linkers couple carboxyls to primary amines or hydrazides, resulting in formation of amide or hydrazone bonds. One widely used carbodiiumide cross-linker is 1-ethyl-3-(3-dimethylaminopropyl)-carbodiimide hydrochloride).

Figure 7:
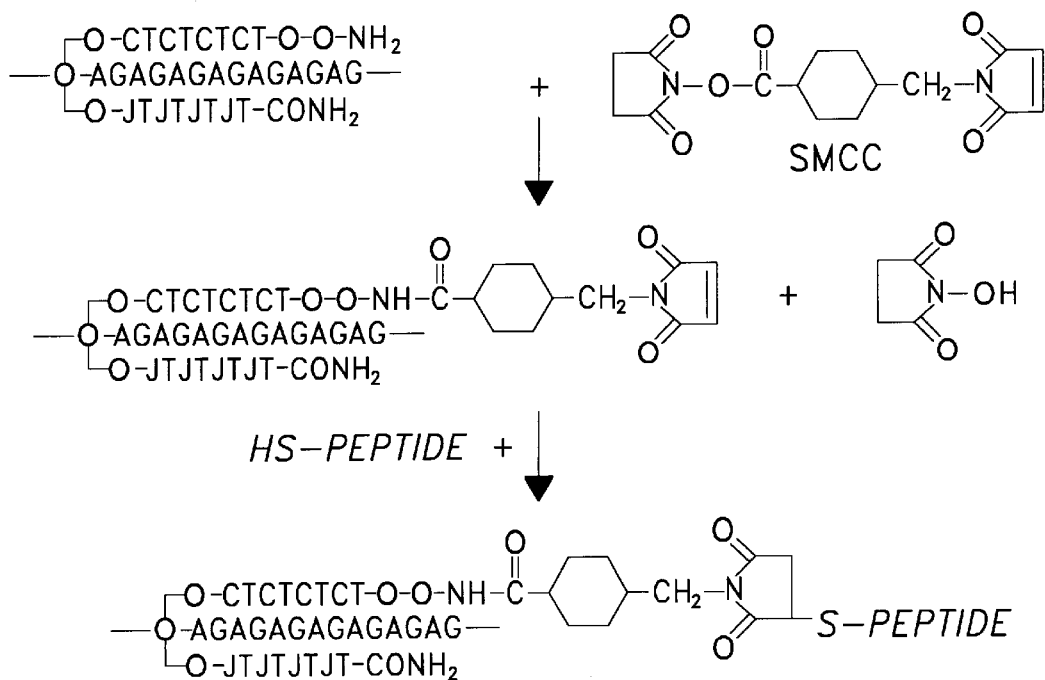
FIG. 7 is a schematic diagram showing the reaction of a PNA clamp with the cross linking agent SMCC, followed by reaction with a peptide sulfhydryl group to form a PNA-peptide bond.

For example, maleimide-labeled PNA is obtained by reacting PNA with SMLCC as discussed in Example 12 and shown in FIG. 7. Pyridydithiol-labeled PNA is obtained by reacting PNA with the crosslinking agent SPDP as discussed in Example 12. Both of these groups react with protein sulfhydryl groups. Any desired chemical group can be conjugated to PNA using conventional chemical methods. The expression vector is then combined with the labeled PNA to produce the research reagent to be used for cell transfection.

The stoichiometry, specificity and reversibility of fluorescent-PNA clamp binding to its complimentary plasmid DNA binding site was characterized as described in Example 1.

EXAMPLE 1

Plasmid Constructs and PNA Molecules

Plasmids—Plasmid VR1060 was constructed by inserting 10 copies of putative PNA binding elements (5'-GAGAGAGA-3'; SEQ ID NO: 1) into a KpnI site of VR1012 (Doh et al., *Gene Ther*. 4:648–663, 1997). The plasmid used as control VR1332 was constructed as described previously (Liang, *Gene Ther*. 3:350–356, 1996). Plasmid pPNA-1-CMV (FIG. 3) was derived from a high-expression vector-based on the human cytomegalovirus (hCMV) immediate early gene (IE) promoter/enhancer plus intron A and bovine growth hormone (BGH) transcription terminator (Doh et al., supra.). The plasmid was constructed by inserting two copies of an oligonucleotide having the sequence:

5' GGTAC-CTCTCTCTCTCTCTCTCTCTCTCTCTCTCTC TCTCTCTCGGTACC3' (SEQ ID NO: 2) into a unique KpnI site located in a non-functional region of the BGH terminator.

Figure 3A:
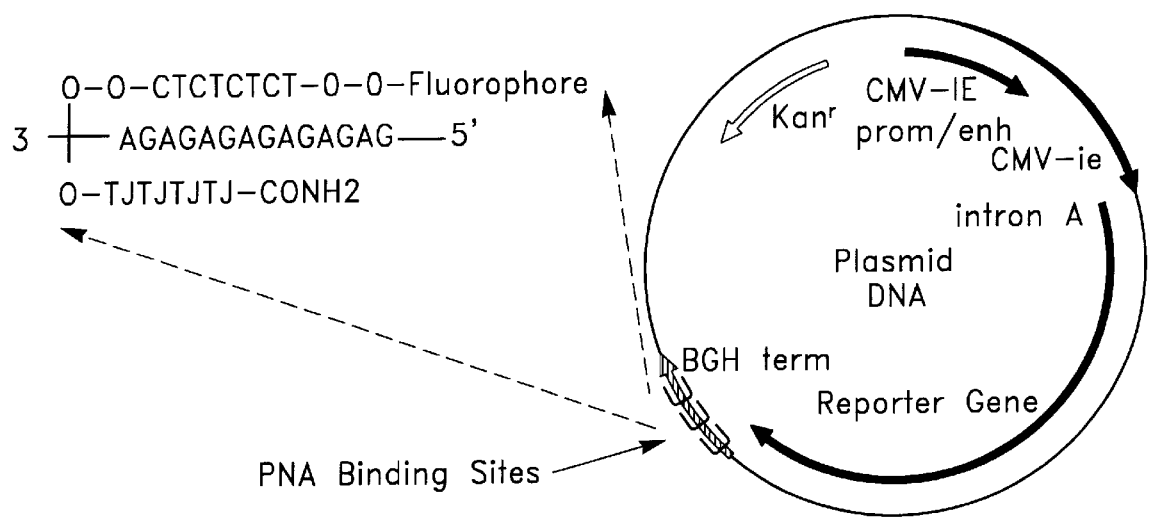
FIG. 3A shows the PNA clamp hybridized to its complementary DNA sequence and pPNA1-CMV plasmid DNA containing PNA binding sites. The PNA clamp hybridizes to the AG-repeat sequences on the plasmid. CMV=human cytomegalovirus; $Kan^R$=kanamycin resistance gene; IE prom/enh=CMV immediate early gene promoter/enhancer region; BGH term=bovine growth hormone gene terminator region.
Figure 3B:
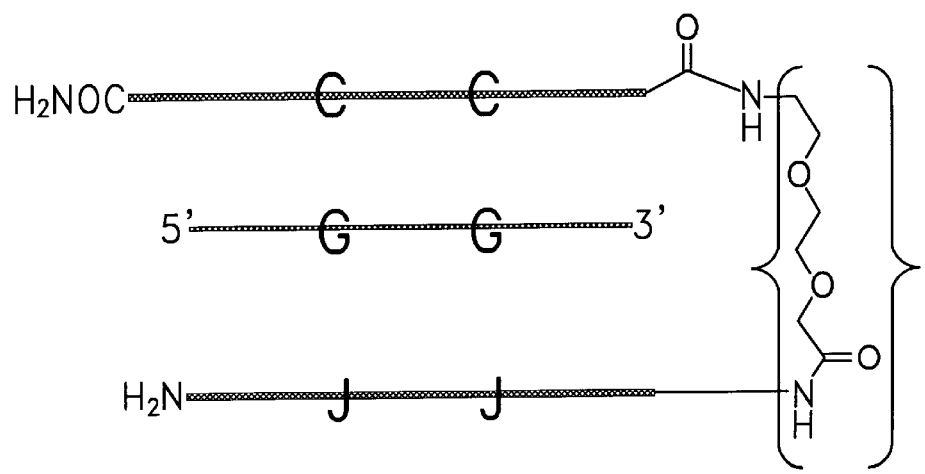
FIG. 3B shows the detailed structure of the O—O—O glycine linker region of the PNA clamp.
Figure 3C:
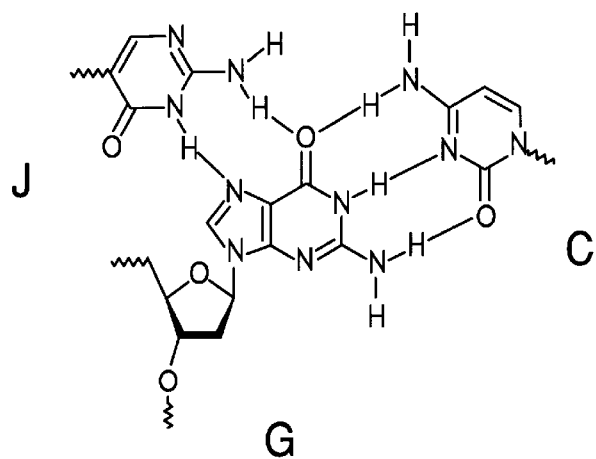
FIG. 3C shows the structure of pseudoisocytosine (J), a cytosine analog, in the PNA clamp.
Figure 3D:
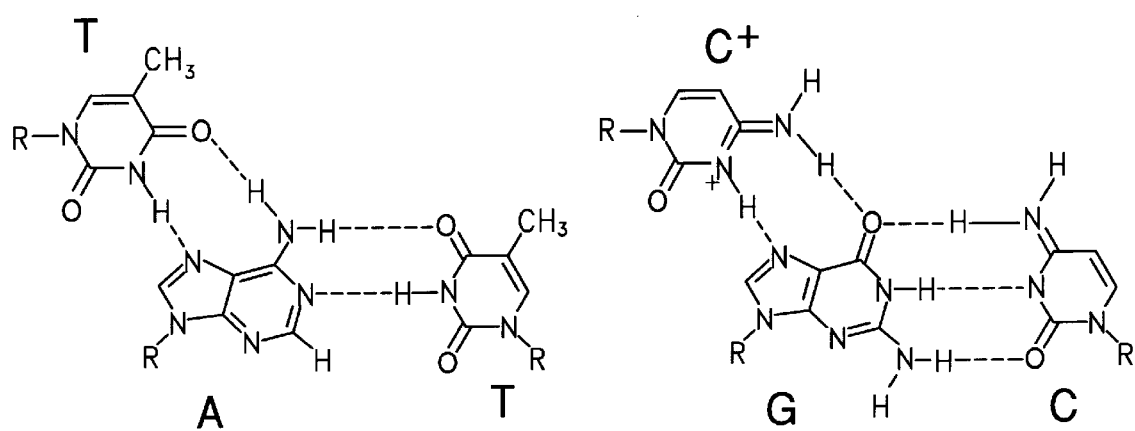
FIG. 3D shows Hoogsteen base pairing between adenine and thymine and protonated cytosine and guanine.

PNA clamps—The PNA used in these studies was designed as a clamp as previously reported (Egholm et al., *Nucl. Acids Res*. 23:217–222, 1995). Rhodamine (Rh), fluorescein (F) or unlabelled PNA containing a terminal primary amino group in place of the fluorophore were purchased from PerSeptive Biosystems (Framingham, Ma.). The PNA sequence used was 5'-TCTCTCTC-O-O-O-JTJTJTJT-3' (SEQ ID NO: 3), where J (pseudoisocytidine) is an analog of C which is optimized to bind in the Hoogstein orientation (Egholm et al. supra., 1995). The "O" residues are 8-aminco-3,6-dioxaoctanoic acid linkers which separate the two regions of the PNA. The PNA is shown in FIG. 3A, along with a plasmid containing regions of DNA complementary to the PNA (PNA binding sites). The linker is shown in detail in FIG. 3B. Pseudoisocytosine, shown in FIG. 3C, is used as a substitute for protonated cysteine, which allows base pairing in the Hoogsteen orientation (FIG. 3D).

A homopurine (or homopyrimidine) binding site, such as this AG(TC) repeat, leads to formation of the PNA-DNA-PNA triplex clamp (Dueholm et al., supra.). Plasmids pPNA1-CMV-LacZ and pPNA1-CMV-GFP were derived by cloning a β-galactosidase gene (Doh et al., supra.) or a mutated green fluorescence protein (GFP) gene (Heim et al., *Nature* 373:663–664, 1995). into the multiple cloning site (MCS) of the vector using standard protocols. Since the homopurine AG insert in the pPNA1-CMV plasmid consisted of 80 nucleotides (two 40 base pair repeats), and each PNA clamp was predicted to hybridize along 8 bases, there were 10 theoretical PNA binding sites per plasmid.

EXAMPLE 2

Assays to Monitor PNA-DNA Hybridization

The hybridization conditions were based on previously published results (Bentin et al., *Biochemistry* 35:8863–8869, 1996; Egholm et al., *Nucleic Acids Res.* 23:217–222, 1995). Plasmid DNA (1.5 µg) in 20 µl was mixed with 1–50 ng of the Rhodamine-labeled PNA (Rh-PNA) in TAE buffer and incubated for 2 hours at 37° C. Then, samples were loaded on 1% TAE agarose gel in the absence of ethidium bromide. Rh-PNA/DNA or fluorescein-PNA/DNA was visualized and photographed under UV light. Following visualization under ethidium bromide-free conditions, the gel was stained with ethidium bromide to localize total plasmid DNA and visualize its integrity. Photographs were scanned using a Silver-Scanner III (LACIE) flat bed scanner The hybridization reaction with both plasmids was monitored by gel electrophoresis. Increasing quantities of PNA were used to determine the point of saturation on the plasmid. Saturation occurred at 8 moles of PNA per mole of plasmid DNA, which is close to the predicted 10 theoretical PNA binding sites per plasmid. Below 8 mole PNA/mole plasmid, there was no evidence of unassociated PNA running at the top of the gel. Above 8 mole PNA/mole plasmid, fluorescent PNA could be detected near the top of the gel. This suggested that the PNA binding site was capable of sequestering all of the available PNA our of the solution, as long as the ratio of added PNA to DNA was less than or equal to 8 mole PNA per mole of plasmid. Therefore, under these conditions, there was no need to remove unbound PNA from the PNA-DNA hybrid.

EXAMPLE 3

Stability of PNA-DNA-PNA Triplex

The stability of the PNA/DNA triplex has been previously characterized in terms of its melting point, but its stability under physiological conditions was not described. In order to evaluate the stability of the PNA-DNA-PNA triplex hybrid, various compounds were added to the preformed triplex and the mixtures were incubated for at least 3 more hours at 37° C. When the Rh-PNA-plasmid hybrid was incubated with a 100 fold molar excess of the phosphorothioate oligodeoxynucleotide (ODN; Genosys Biotechnologies, Inc., The Woodlands, Tex.) containing the PNA binding site (5'-CCCCTTGGTAGAGAGAGAGA-3'; SEQ ID NO: 4), Rh-PNA was not displaced from the plasmid. When a control plasmid (without the PNA binding site) was incubated with the Rh-PNA and a 100 fold molar excess of ODN was subsequently added, Rh-PNA could be seen associated with the ODN. These results showed that the PNA/DNA triplex, once formed, was not freely reversible.

In order to further assess the stability of the PNA/DNA hybrid clamp, a fluorescence resonance energy transfer (FRET) assay was developed which could monitor binding of the PNA to its DNA binding site as described in Example 4.

EXAMPLE 4

Fluorescence Resonance Energy Transfer (FRET) Assay

FRET has been previously used to monitor the formation and dissociation of lipoplexes, the hybridization of complimentary ODNs and the formation of triple helices (Zelphati et al., *Proc. Natl. Acad. Sci. U.S.A.* 93:11493–11498, 1996; Sixou et al., *Nucl. Acids res.* 22:662–668, 1994; Mergny et al., *Biochemistry* 33:15321–15328, 1994). The FRET signal is based on energy transfer between a fluorescent donor (F-ODN) and a fluorescent acceptor (Rh-PNA) and it is characterized by quenching (Q) of the fluorescein emission.

The ODN was either labeled with fluorescein (F-ODN) at its 3'-end or left unlabeled. Fluorescence measurements were performed and fluorescein fluorescence quenching (Q) was calculated as described (Sixou et al., supra.). Unlabeled or F-ODN were mixed with unlabeled or Rh-PNA in hybridization buffer (100 mM NaCl, 10 mM Na-phosphate, 1 mM EDTA, pH 7.0) as described (Egholm et al., *Nature* 365:566–568, 1993). After 2 hours of incubation at 37° C., various compounds (See FIG. 4) were added to the preformed triplex and the mixtures were incubated for at least 3 more hours at 37° C. Emission spectra were recorded between 500 and 600 nm with λ.ex=470 nm. Fluorescence was measured with a SPEX 1680 spectrofluorometer (Spex Industries, Edison, N.J.).

Figure 4:
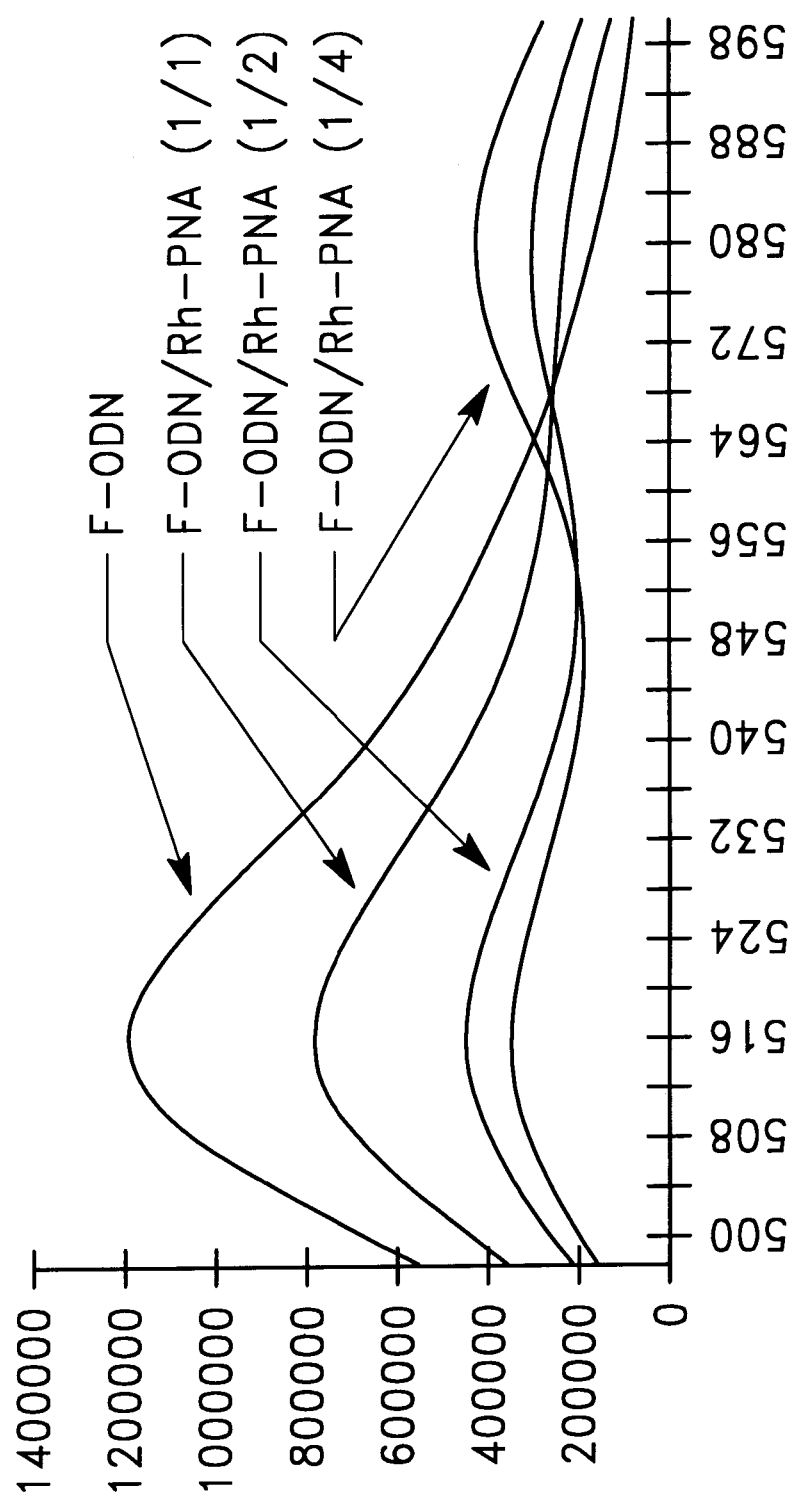
FIG. 4 shows the characterization of PNA/oligodeoxynucleotide binding by fluorescent resonance energy transfer (FRET) in the presence of increasing amounts of rhodamine-labeled PNA.

The donor alone (F-ODN) incubated with unlabeled PNA, as well as the acceptor alone (Rh-PNA) incubated with the unlabeled donor, showed no significant changes in the emission spectra. In contrast, when F-ODN and Rh-PNA were mixed, the fluorescein emission was specifically quenched (Q=75–80%; FIG. 4). Maximum fluorescence quenching occurred at the expected stoichiometry of 1 PNA clamp per ODN binding site. When a different F-ODN was used that did not contain the PNA binding sequence, there was no significant fluorescein quenching. These results established that the FRET assay could be used to monitor the PNA to ODN hybridization reaction.

Figure 5:
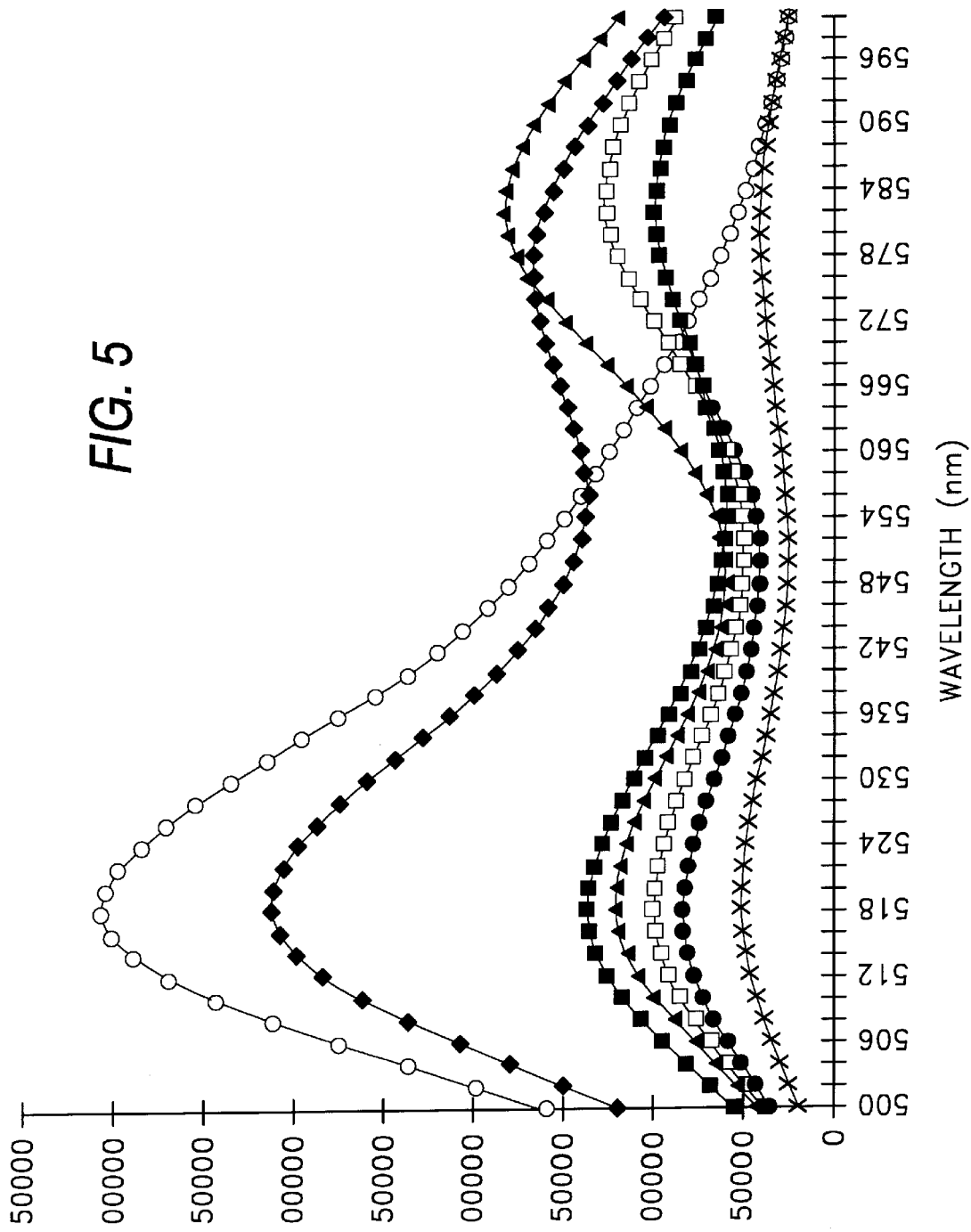
FIG. 5 shows ODN/PNA association and dissociation characterized by FRET. (●)F-ODN alone; (○) F-ODN/Rh-PNA; (□) triplex+1000X weight excess of salmon sperm DNA; (■) triplex+1000X molar excess of competitive ODN; (x) triplex+100X molar excess of DMRIE:DOPE lipids; (▲) triplex+1000X weight excess of histones and (♦) NaCl/SDS treatment (incubation of the PNA/ODN triplex in 50mM Tris-HCl, 500 mM NaCl, 10 mM EDTA pH 8.9, 1% SDS) for 45 min at 58° C.

The stability of the preformed Rh-PNA/F-ODN hybrid in the presence of a large excess of various agents was determined by measuring the change in fluorescein quenching (Q) after incubation for 3 hours at 37° C. (FIG. 5). None of the compounds tested were able to dissociate the triplex formed between F-ODN and Rh-PNA, as measured by the FRET assay (Table 1). Charged and neutral lipids, plasmid DNA containing the PNA binding sites, tRNA, dATP, polyglutamic acid, BSA, dextran and heparin sulfate, spermine, spermidine and polylysine added in very large molar excess did not destabilize the PNA triplex clamp. In fact, only a very strong saline/detergent treatment at elevated temperature was able to reverse the association (FIG. 5; Table 1). Thus, the PNA/DNA triplex is very stable in the presence of synthetic or cellular compounds and even a competitive excess of DNA or ODN was not able to dissociate the triplex clamp from its binding site.

TABLE 1

Effect of various biomolecules on PNA/ODN stability

|  | Ratio | Q (%) | DQ (%) |
|---|---|---|---|
| F-ODN/Rh-PNA |  | 79.5 | 0 |
| PS:DOPE | 100 (m) | 66.5 | 16.3 |
| PG:DOPE | 100 (m) | 74.5 | 6.3 |
| DOPE | 100 (m) | 73 | 8.3 |
| DOPC | 100 (m) | 75 | 6.2 |
| DMRIE:DOPE | 100 (m) | 87 | −9.8 |
| salm. sperm DNA | 10000 (w) | 75.4 | 5.2 |
| VR1060 | 25 (m) | 68.7 | 13.6 |
| ODN | 1000 (m) | 66.2 | 16.7 |
| tRNA | 1000 (w) | 72.5 | 9.2 |
| dATP | 5000 (m) | 75.9 | 4.6 |
| Polyglutamic Acid | 5000 (m) | 73.5 | 7.5 |
| BSA | 20000 (w) | 96.3 | −21 |
| Dextran Sulfate | 1000 (m) | 76.8 | 3.4 |
| Heparin Sulfate | 1000 (w) | 76.2 | 4.2 |
| Spermine | 5000 (m) | 73.8 | 7.2 |
| Spermidine | 5000 (m) | 68.6 | 13.7 |
| Histones | 1000 (w) | 70 | 11 |
| Polysine | 1000 (m) | 74 | 7 |
| NaCl/SDS |  | 23 | 70.8 |

Since it has been demonstrated that binding of PNA to duplex DNA can create an open D-loop of the opposite strand (Cherny et al., *Proc. Natl. Acad Sci. U.S.A.* 90:1667–1670, 1993; Almarsson et al., *Proc. Natl. Acad. Sci. U.S.A.* 90:9542–9546, 1993), the nuclease sensitivity of the plasmid might have been modified by the presence of the PNA. This effect was previously shown for a linearized plasmid (Demidov et al., *Nucl. Acids Res.* 21:2103–2107, 1993). Thus, the nuclease sensitivity of the supercoiled plasmid DNA with or without PNA was compared as described in Example 5.

EXAMPLE 5

Nuclease Sensitivity of Plasmid DNA Containing PNA Probe

PNA/DNA triplexes were prepared and analyzed as described in Example 1. Samples were then treated with 1 unit of restriction endonucleases, 10 units of S1 nuclease or 0.1 units of DNase I. For S1 nuclease and DNase I assay, the reactions were stopped by adding 3 µl of 0.5 M EDTA, pH 8 and samples were rapidly frozen.

In all nuclease digestion experiments conducted with restriction enzymes, S1 nucleases and DNase I, no differences were observed in the kinetics or extent of digestion when PNA was bound to the supercoiled plasmid DNA. Thus, PNA binding did not alter the nuclease sensitivity of supercoiled plasmid DNA.

Another criteria for an effective plasmid probe is that it should not affect the biological activity (level of reporter gene expression) of the plasmid. We therefore transfected several cell lines with the cationic lipids DMRIE/DOPE in which the plasmid was either hybridized with the fluorescent PNA clamp or left unhybridized as described in the following example.

EXAMPLE 6

In Vitro Transfection Assay

The synthesis of the cationic lipid 1,2-dimyristyloxypropyl-3-dimethyl-hydroxyethyl ammonium bromide (DMRIE), the DMRIE:DOPE (1:1 molar ratio) lipid film/liposome preparation and transfection were performed as reported (Felgner et al., *J. Biol. Chem.* 269:2550–2561, 1994). Briefly, fluorescently-labeled liposomes were prepared by incorporating 1 mole percent of 1,2-dioleoyl-sn-glycero-3-phosphatidylethanolamine-N-(lissamnine rhodamine B sulfonyl) (N-Rh-PE) into the cationic lipid formulations. The fluorescent lipid was mixed in chloroform together with the other lipids in the formulation before producing the dried lipid film. For the production of large multilamellar vesicles (MLV), the dried lipid film was rehydrated by adding the appropriate vehicle (i.e. distilled water, 0.9% saline or 5% sorbitol/20 mM sodium acetate, pH 6 buffer) in order to obtain a lipid concentration of 1 mM-4 mM. The vials were vortexed continuously for two minutes at the highest setting using a foam platform attached to a Genie-2 vortexer to produce the MLV.

For lipoplex preparation, one volume of cationic liposomes were mixed with one volume of DNA. DNA and cationic liposomes were mixed together al 0.5 DMRIE/DNA molar ratio (mole or positive charge equivalents of the cationic lipids per negative charge equivalent or mole of DNA phosphate) and used within 2 hours after mixing.

B16F10 (mouse melanoma, ATCC CRL 6322), CV-1 (African Green monkey kidney, ATCC CCL 70) and COS-7 (African Green monkey SV40 transformed kidney) were grown in DMEM containing 10% fetal bovine serum and antibiotics. These cells were transfected by lipoplexes (VR1062 plasmid DNA complexed to DMRIE:DOPE cationic liposomes) in 96-well plates in OptiMEM™ media (GIBCO Life Technologies, Inc.). VR1062 plasmid was constructed by cloning a β-galactosidase gene into the VR1060 vector (Doh et al., *Gene Ther.* 4:648–663, 1997).

The β-galactosidase assay is performed as follows. Because β-galactosidase is not a secreted protein, the culture media was aspirated post-transfection, the transfected cells were lysed with 50 µl lysis buffer (250 mM Tris, pH 8.0, 0.1% Triton X-100), then subjected to one freeze/thaw cycle (freeze at −70° C. and thaw at room temperature). While the cells were being lysed, a β-galactosidase (*E. coli* from Sigma) standard curve was prepared in a fresh 96-well U-bottom plate with 5% BSA in PBS (w/v). Once the plate of lysed cells was completely thawed, a 50 µl aliquot of each point on the standard curve was transferred to control wells of the plate—the highest amount of β-galactosidase is 40,000 pg. The color is obtained by the addition of 150 µl of 1 mg/ml of Chlorophenol red-β-D-galactopyranoside (CPRG, Boehringer Mannheim) dissolved in β-gal buffer (1 mM $MgCl_2$, 10 mM KCl, 50 mM β-mercaptoethanol, 60 mM $Na_2HPO_4$, pH 8.0). The reaction is allowed to incubate at room temperature for 10 minutes to 4 hours, depending on the cell type, and the absorbance readings are taken at 580 nm using the Vmax Microplate Reader.

Figure 6:
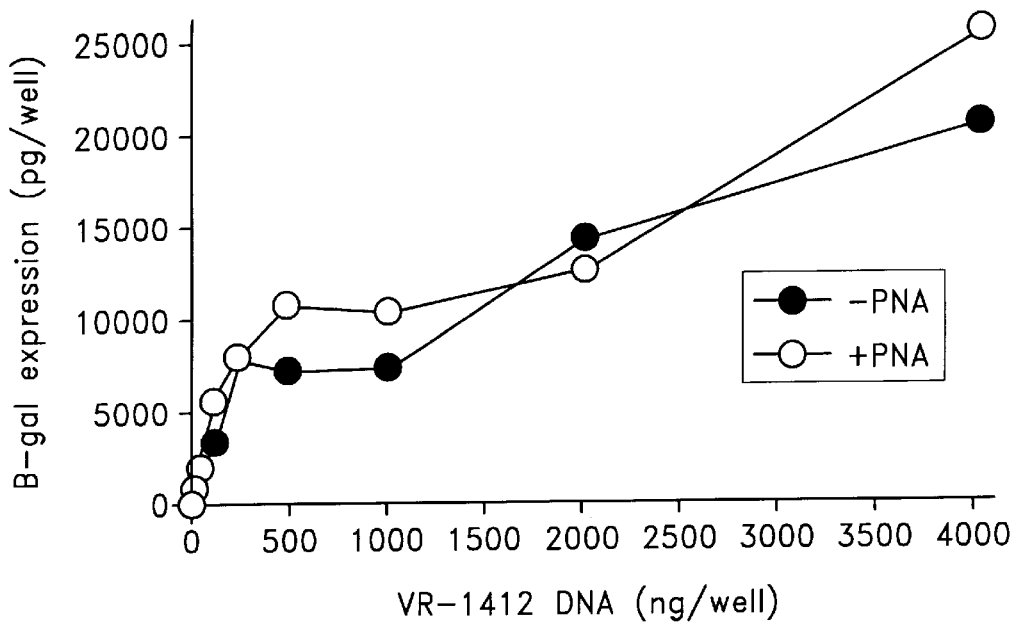
FIG. 6 shows the transfection activity of pPNA1-CMV-β-gal with and without bound PNA.

In all cell lines examined (CV-1, B16F10, COS 7), the level of reporter gene expression (VR 1062; β-galactosidase) was the same regardless of whether the PNA was associated with the plasmid. The results for pPNA1-CMV-βgal with and without bound PNA is shown in FIG. 6. Furthermore, the expression of a second plasmid encoding GFP was not affected by PNA binding. Thus, PNA binding does not affect biological activity of the plasmid.

To determine whether fluorescent PNA hybridized to an oligonucleotide would affect intracellular trafficking of the oligonucleotide, the following experiment was performed.

EXAMPLE 7

Intracellular Localization of ODN, ODN/PNA and Lipids

F-ODN (0.5 μg) alone or hybridized to Rh-PNA and then complexed to cationic liposomes comprising DMRIE:DOPE were incubated in serum free medium on CV-1 cells grown on coverslips. After 3 hours at 37° C., medium containing 10% FBS was added, and cells were washed 3 times with phosphate buffered saline (PBS) and mounted on hanging drop slides (Fisher Scientific) with PBS. Cells were immediately examined with an upright fluorescent microscope (Nikon, Optiphot) equipped with a 60X oil immersion objective and 3 CCD camera video system (Carl Zeiss). Images were captured by using the Kontron KS-400 image analysis software (Kontron Elektronik).

When CV-1 cells were incubated with naked Rh-PNA labeled plasmid (i.e., in the absence of cationic lipid, only a low level of punctate cytoplasmic fluorescence was observed and no nuclear localized fluorescence was seen. When cationic lipids were used to deliver the fluorescent plasmid, a greatly increased amount of fluorescence was associated with the cells, but none was present in the nuclei after 3 hours of incubation. The detection of Rh-PNA labeled plasmid in the nucleus was observed only after an overnight incubation (16–24 hours). There was a marked difference in the extent and kinetics of nuclear uptake between ODN which showed considerable nuclear uptake within 3 hours post-transfection and plasmid DNA. Based on previously published results, cell division does not appear to be required for intracellular ODN delivery, since ODN enter the nucleus very rapidly and nuclear accumulation of ODN is a temperature- and energy-independent process (Chin et al., *New Biol.* 2:1091–1100, 1991; Leonetti et al., *Proc. Natl. Acad. Sci. U.S.A.* 88:2702–2706, 1991). In contrast, nuclear uptake of plasmid DNA required overnight incubation, suggesting that cell division may be required.

Since nuclear accumulation of the fluorescent PNA label was seen only after an overnight incubation, it was particularly important to determine whether the observed fluorescent signal was derived from the intact plasmid or from degraded DNA fragments. To address this question, plasmid degradation in transfected (CV-1 cells was followed as a function of time on the DNA extracted from these transfected cells as described in the following example.

EXAMPLE 8

Integrity of Transfected PNA-Labeled Plasmid DNA

CV-1 cells ($2\times10^5$ cells) plated in 6-well plates were transfected with 5 μg DNA per well and complexed to DMRIE:DOPE as previously described (Felgner et al., *J. Biol. Chem.* 269:2550–2561, 1996). After various incubation times, culture medium was removed, cells were washed twice with PBS and treated at room temperature for 15 minutes with PBS/dextran sulfate buffer (1 mg/ml) to remove extracellular cationic lipid/DNA complexes. After two washes, cells were trypsinized, centrifuged and lysed. DNA extraction and Southern blotting were performed according to standard procedures. The DIG non-radioactive nucleic labeling and detection system (Boehringer Mannheim) were used as described by the manufacturer. Blank plasmid DNA, without the coding sequence, was used as a probe and labeled by random priming with the DIG kit.

When cells were transfected at 4° C., considerable uptake onto the cell surface occurred, but no intracellular entry of liposomes or DNA occurred. Cell surface associated plasmid DNA could be recovered from cells that were transfected and incubated at 4° C. Cell surface associated DNA could be removed by washing the transfected cells with the dextran sulfate/PBS buffer. Southern blot analysis showed that most of the intracellular plasmid DNA delivered by the cationic lipid DMRIE was still intact even 48 hours after transfection. After 24 hours, the amount of intracellular plasmid recovered was estimated to be 3–5% of the total input DNA which represents an average of 30,000–50,000 copies of plasmid/cell. When the blot was exposed for a longer time period, a small amount (<2% of the total plasmid) of degraded plasmid could be detected as smaller fragments running as a-smear ahead of the supercoiled band. These results strongly suggest that most of the fluorescence observed in cells corresponds to intact DNA.

The utility of the PNA probe for following the biodistribution of double stranded DNA was examined. As observed for single stranded DNA, the presence of PNA on ODN duplex did not modify the intracellular localization or kinetics of cationic lipid mediated duplex ODN delivery. Duplex ODN delivered by cationic lipids were also taken up by the nuclei, and the PNA did not modify the intracellular localization of either the duplex ODN or the lipids. Moreover, whether the fluorophlore was linked to the PNA or to the ODN the intracellular trafficking was the same. These results with duplex DNA and those described above for single stranded DNA support the use of the PNA probe for following biodistribution of fluorescent-PNA labeled duplex plasmid in viable cells.

The intracellular localization of plasmid DNA using the fluorescent-PNA probe was monitored as described in Example 9.

EXAMPLE 9

Intracellular Localization of Plasmid DNA

The use of GFP has been shown to be a useful and rapid method for monitoring gene transfer in viable cells. Two plasmids were used in this study, VR1060 as described in Example 1 and VR1461 plasmid was derived by cloning a mutated GFP gene (Heim et al., *Nature* 373:663–664, 1995) into the VR1060 vector. Cells were treated as described in Example 7. When CV-1 cells were incubated with naked Rh-PNA labeled plasmid (i.e. in the absence of cationic lipid), only punctate cytoplasmic fluorescence was observed, and no nuclear localized DNA was observed. Complexation with cationic liposomes greatly increased the uptake of fluorescent plasmid as seen by the higher fluorescence intensity per field. However, in contrast to what was observed with ODN, no plasmid was present in cell nuclei after 3 hours of incubation. The detection of nuclear Rh-PNA labeled plasmid was observed only after an overnight incubation (from 16 to 24 hours). Co-localization of lipid and DNA was apparent on the cell surface and in intracellular punctate structures, but lipids were never observed in the nuclei.

In order to confirm that fluorescent plasmid localized in the cell nuclei was biologically active and not degraded, Rh-PNA labeled plasmid encoding GFP was transfected into CV-1 cells. With this system plasmid delivery could be monitored by using a red filter, and protein expression could be independently monitored under a green filter. The results showed that all cells expressing GFP had fluorescent plasmid in the nucleus and no GFP was detected in cells that lacked fluorescent nuclear plasmid. However, some cells which contained nuclear fluorescent plasmid were negative for GFP. In a previous report where FISH and immunochemistry was used together to detect DNA and its gene products in transfected cells (Gussoni, *Nature Biotechnol.* 14:1012–1015, 1996), it was also concluded that some cells could contain nuclear DNA while they were negative for gene expression. There are at least three possible explanations for this observation: i) the DNA is inactivated or degraded in as small number of cells, ii) too many copies of nuclear plasmid leads to transcription factor competition and inhibition of expression, or iii) plasmid just entering the nucleus has not yet had enough time to accumulate a sufficient GFP signal.

All steps required to validate the use of the fluorescent PNA clamp as a probe to follow plasmid biodistribution have been characterized. The fluorescent plasmid is not significantly altered in terms of physical and biological properties. In contrast to DNA intercalating dyes, the PNA binding is sequence-specific and extremely stable under physiological conditions. The presence of PNA on single or double stranded nucleic acids does not modify their nuclear uptake. The majority of the intracellular plasmid following cationic lipid mediated transfection remains conformationally intact, and the intranuclear plasmid is biologically active. Finally, all cells expressing GFP also contain easily detectable fluorescent-DNA in their nuclei, and the system is sensitive enough to show that all cells lacking fluorescent plasmid are also GFP negative.

The use of the fluorescent PNA and GFP as a means of following plasmid distribution and expression, has advantages over approaches which utilize FISH and immunochemistry. FISH requires the tissue to be fixed, sectioned and permeabilized, and it is restricted by parameters such as probe sizes, tissue section thickness and fixation methods (Gussoni, *Nature Biotechnol.* 14:1012–1015, 1996). The fluorescent PNA can be used in viable cells in real-time to identify the elements in the cytoplasmic network that restrict nuclear entry. (Dowty et al., *Proc. Natl. Acad. Sci. U.S.A.* 92:4572–4576, 1995). The amount of fluorescent plasmid in the various intracellular compartments of the cell can also be quantified by using image analysis software.

Because of its versatility, convenience and rapid detection, fluorescent-PNA labeled plasmid is a powerful tool to study factors affecting plasmid biodistribution. The combined use of GFP and fluorescent PNA will provide a better understanding of the factors that influence the potency of non-viral gene delivery systems for human gene therapy applications.

EXAMPLE 10

Analytical Quality Control Assays for Production of PNA-Labeled Plasmids

The present invention includes novel research reagents comprising PNA conjugates irreversibly hybridized to plasmid DNA. To ensure that the individuals who purchase these reagents receive a reproducible product, quantitative analytical assays indicative of activity and stability of the product are performed as described below.

Preparation of a fluorescent PNA-DNA hybrid—The initial PNA-DNA hybridization conditions are 50 μg of plasmid DNA (15 pmoles) mixed with fluorescent-labeled PNA (8 fold molar excess=120 pmoles) in a total of 100 μl of various buffers and incubated for 2 hours at 37° C. These initial conditions may be routinely optimized with respect to buffer composition (ionic strength and pH), DNA and PNA concentrations, incubation time and temperature.

Agarose gel electrophoresis—Agarose gel electrophoresis is used to monitor plasmid integrity, conformation changes, aggregation and product losses which may occur during storage of the PNA labeled plasmid. Freshly prepared, frozen, or stored plasmid DNA labeled with a fluorescent PNA probe (2 μg) is analyzed on a 1% agarose gel in TAE buffer. Fluorescent PNA-DNA is visualized and photographed under UV light. The gel is subsequently stained with ethidium bromide to visualize total DNA and photographed under UV light. Photographs are scanned using a SilverScanner III (LACIE) flat bed scanner.

Optical density and fluorescence intensity measurements—An aliquot of the PNA-plasmid hybrid, manufactured and stored under different conditions, are taken to determine the total quantity of DNA recovered and the total quantity of fluorescent PNA recovered. Measurements at an optical density (OD) of 260 nm are taken with a Shimadzu spectrophotometer Model UV-1601. Fluorescence is measured with a FluoroMax 2 spectrofluorometer (SPEX instruments). Acceptable manufacturing conditions result in good recovery of total DNA based on the optical density measurements, and PNA based on the total fluorescence signal.

In vitro transfection activity—In vitro transfection assays are used to determine the biological activity of the fluorescent PNA labeled plasmids after storage essentially as described in Example 6. Serial dilutions of the DMRIE-DNA lipoplexes are performed as follows: OptiMEM™ (75 μl) is placed in each well of an empty 96-well plate, then 75 μl of the lipoplexes are transferred to the first well of each row and two fold dilutions are performed from column 1 to 12. Next, 75 μl of OptiMEM™ is dispensed into each well and 100 μl of this mixture is transferred to the wells of a 96-well plate containing cells.

For transfection conducted with plasmids encoding heat stable secreted alkaline phosphatase (SEAP), alkaline phosphatase assays are done as follows. Supernatants from transfected cells are heated at 65° C. for 30 minutes to inactivate background endogenous alkaline phosphatase activity without inactivating the SEAP transgene. Forty-eight hours post-transfection, aliquots of the culture media are taken and the SEAP activity is quantitatively determined using a colorimetric assay based on hydrolysis of the chromogenic substrate para-nitrophenyl phosphate (PNPP). PNPP reagent (0.1% w/v) is dissolved in 1 mM $MgCl_2$, 1 M diethanolamine, pH 9.8. Into each well of a 96-well plate, 10 μl of 0.05 Zwittergent in PBS ($Ca^{2+}$ and $Mg^{2+}$-free, GIBCO) is added, followed by addition of 20 μl heated cell culture media to each well. For control wells, 20 μl water is used to normalize the volume. An alkaline phosphatase (AP) standard (EIA grade calf intestine AP; Boehringer Mannheim) is used to generate a standard curve from 1 to 100 pg per well. The PNPP substrate (200 μl) is added to each well to start the enzymatic reaction. The reaction is allowed to stand at room temperature for 30–45 minutes prior to analysis. The use of 0.05% Zwittergent in PBS as the diluent virtually reduces the background to zero, which increases to detection limit of the assay. The plates are read with a Vmax MicroPlate reader from Molecular Devices (Palo Alto, Calif.) with the wavelength set at 405 nm using either kinetic or static readings. For plasmids encoding β-galactosidase, the assay is run as described in Example 6. For plasmids encoding luciferase and chloramphenicol acetyltransferase (CAT), luciferase and CAT assays are performed as described (Wheeler et al., *Proc. Natl. Acad. Sci. U.S.A.* 93:11454–11459, 19916).

Fluorescent microscopy studies—The intracellular trafficking of freshly prepared fluorescent plasmid is compared with a plasmid retained for different amounts of time under different storage conditions as described in Example 7.

EXAMPLE 11

Effect of Storage Conditions on Fluorescent PNA Labeled Plasmids

The fluorescent PNA/DNA prepared as described hereinabove is stored at −70° C., −20° C., room temperature, and at 2–8° C. in various buffers, or lyophilized. DNA preparations are stored in 100 μg/ml, 500 μg/ml and 1 mg/ml in 100 μl aliquots. The vehicles used are water, 50% glycerol, 10% sucrose, 5% sorbitol, TAE, TE, PBS, sodium phosphate, HEPES-buffered saline and Tris-NaCl buffer. Biological activity is determined based on in vitro transfection assays and fluorescence microscopy. Stability studies are conducted according to the following matrix (Table 2), following the stabilities as a function of the amount of time in storage.

TABLE 2

| Temp/Time | Initial | 2 week | 6 week | 3 month | 8 month | 9 month | 12 month | End |
|---|---|---|---|---|---|---|---|---|
| −70° C. | | X | | X | X | | X | X |
| −20° C. | | X | X | X | X | X | X | X |
| 2–8° C. | X | X | X | X | X | X | X | X |
| RT | | X | X | X | X | | | |

Following identification of manufacturing conditions leading to a product with acceptable shelf life, an inventory of plasmid products is generated. Representative examples of such products are shown in Table 3. It is not necessary to offer the fluorescein labeled GFP construct since fluorescein and GFP fluoresce with essentially the same color. These products are placed in 25 μg and 100 μg unit vials. these quantities are sufficient to conduct in vitro transfection assays and in vivo biodistribution studies.

TABLE 3

| | | Reporter Gene | | | | |
|---|---|---|---|---|---|---|
| Label | Blank | β-Galactosidase | Green Fluorescent Protein | Secreted Alkaline Phosphatase | Luciferase | CAT |
| Rhodamine | X | X | X | X | X | X |
| Fluorescein | X | X | | | X | X |
| Biotin | X | X | X | X | X | X |

The examples described above relate to PNA probes labeled with fluorophores. The examples presented below describe conjugation of peptides to PNA and the use of these conjugates. In an alternative embodiment, peptides are linked directly to PNA by the commercial supplier, and these PNAs carrying the peptide motif are hybridized directly to the plasmid containing the PNA binding site.

EXAMPLE 12

Coupling of Peptides to PNA

Heterobifunctional conjugation reagents such as SPDP ([N-succinimidyl 3-(2-pyridyldithio)propionate) and SMCC (succinimidyl 4-(N-maleimidomethyl) cyclohexne-1-carboxylate) contain two different reactive functional groups. SPDP and SMCC are obtained from Pierce (Rockford, Ill.). The chemical targets of these reagents are the amine-reactive end of the glycine on the PNA (5') and the sulfhydryl-reactive end of a cysteine present on the peptide. The coupling reaction results in a direct cross-link between the PNA and the peptides. Two approaches are contemplated for peptide conjugation: modification of the amino PNA after its hybridization to DNA, or peptide conjugation to PNA followed by hybridization of the conjugate to the plasmid. In a preferred embodiment, a plurality of 8-amino-3,6-dioxaoctanoic acid linkers, preferably 2 or 3, is added to the 5' end of the PNA to increase coupling efficiency.

SPDP—The activated NHS ester end of the SPDP reagent reacts with the amino groups (5' end glycine) on PNA to form an amide linkage. The 2-pyridyldithiol -group at the other end reacts with the sulfhydryl residue to form a disulfide linkage with the sulfhydryl-containing peptide. To the PNA/DNA solution prepared in PBS, pH 7.5 (PNA is already hybridized to DNA), is added 10–20 molar excess of SPDP (20 mM stock solution in DMSO) over the amount of PNA present. After a 1 hour incubation at room temperature, the modified PNA/DNA is purified by gel filtration on a Sephadex G-50 column to remove excess crosslinker and reaction by-products. Fractions are collected and peak fractions containing the DNA are pooled. The SPDP-derivatized PNA/plasmid hybrid is concentrated with a microconcentrator or by isopropanol precipitation.

To determine the efficiency of the modification, an aliquot of the SPDP-derivatized PNA/DNA is treated with dithiothreitol (DTT; 25 mM for 30 minutes at room temperature) to release the pyridine-2-thione group. The release of pyridine-2-thione is measured spectrophotometrically at 343 nm ($\epsilon=8\times10^3$ $M^{-1}cm^{-1}$) to quantify the amount of sulfhydryl modification (PNA modified by SPDP).

SMCC—The activated NHS ester end of the SMCC reagent reacts with primary amino groups (5' end glycine) on the PNA to form a stable amide bond. The maleimide at the other end couples to the sulfhydryl residue of the peptide. The reaction of PNA with SMCC and peptide is shown schematically in FIG. 7.

To the PNA/DNA solution in 100 mM sodium phosphate, 150 mM NaCl, 1 mM EDTA pH 7.2 or PBS, pH 7.2 (PNA is already hybridized to DNA), is added 40–80 fold molar excess of SMCC (20 mM stock solution in DMSO) over the amount of PNA present. After incubation for 1 hour at room temperature with periodic mixing, the maleimide-activated PNA/DNA is purified to remove the excess crosslinker and reaction by-products by gel filtration on a Sephadex G-50 column equilibrated with 100 mM sodium phosphate, 150 mM NaCl, pH 7.2 or PBS, pH 7.2. Fractions are collected and the peak fractions containing the DNA are pooled. The SMCC-derivatized PNA/DNA is then concentrated with a microconcentrator or by isopropanol precipitation.

To determine the efficiency of the modification, the amount of maleimide-activated PNA/DNA is quantified by a fluorescamine assay and by Ellman's reagent. After coupling the synthetic peptide to the DNA/PNA via the heterobifunctional crosslinking agent (SMCC or SPDP), the elution profile is monitored by either the disappearance of the fluorescamine signal or the colorimetric reaction of dithiobisnitrobenzoic acid (Ellman's reagent) with the free sulfhydryl residues of the terminal cysteine on the peptide.

EXAMPLE 13

Quantification of Reduced Sulfhydrals and Primary Amino Groups

Coupled and free peptides are separated by column chromatography. Sephadex G-50 is packed into a 0.7×15 Econo-Column from BioRad (Hercules, Calif.) and equilibrated with PBS, pH 7.4. One ml fractions are collected. A 10–50 µl aliquot of each eluted fraction is added to 1 ml of 5 mM EDTA in PBS, pH 7.4, followed by 100 µl of 1 mM Ellman's reagent dissolved in methanol. Fractions containing free sulfhydryl residues, which produce a bright yellow color, are pooled and quantified by taking an absorbance reading at 412 nm using a BioSpec-1601 spectrophotometer (Shimadzu, Columbia, Md.). L-cysteine or glutathione is used to prepare the standard curve.

The coupling of the aminoPNA to the heterobifunctional linker is quantified by reacting the primary amine on the PNA with the fluorogenic reagent fluorescamine. Two milliliters of assay buffer (sodium borate, pH 9.2) is delivered into 12×75 borosilicate glass test tubes. A solution of aminoPNA to be assayed with and without linker is added to the borate buffer at a level of amine sufficient to give a signal-to-noise ratio of at least 10. Fluorescamine obtained from Aldrich Chemical Co. (Milwaukee, Wis.) is dissolved in acetone to a final concentration of 1.5 mM in a screw cap glass tube. While vortexing vigorously (without splashing), 200 µl of the fluorescamine reagent is added to the aminoPNA solutions to ensure complete mixing. The samples are then transferred to 10 ml polystyrene cuvettes and the fluorescence is measured at room temperature using the FluoroMax (SPEX Instruments) with the $\lambda$ex=392 nm and the $\lambda$em=480 nm. The slits for both wavelengths are set at 2.5 mm. The time based scan mode is used with the integration time of 5 seconds. A reading is taken after the signal is stable (about 20 sec). A blanking solution is used to correct for background. Plasmid DNA and the bifunctional linkers alone do not react with fluorescamine.

EXAMPLE 14

Coupling of Fluorescent Peptides to the Conjugated PNA-Plasmid Hybrid

Several different peptides containing a nuclear localization sequence, a fusogenic amphipathic peptide, or a receptor specific ligand sequence are obtained from Multiple Peptide Systems or Sigma. Each peptide contains a cysteine at one end in order to react with the SPDP or SMCC modified-PNA/DNA. In some cases, a fluorescent peptide is used to follow the conjugation reaction.

To label peptides with a fluorophore, two different amine-reactive fluorophore derivatives are used: fluorescein isothiocyanate (FITC) and tetramethylrhodamine-5- (and 6)-isothiocyanate (TRITC) obtained from Molecular Probes (Junction City, Oreg.). These reagents react under alkaline conditions with primary amines in peptides to form stable, highly fluorescent derivatives.

A peptide solution in 100 mM sodium carbonate, pH 9, at a concentration of at least 2 mg/ml is prepared. FITC and TRITC (1 mg/ml in DMSO) are protected from light and slowly added to the peptide solution (50 µl fluorophore/ml peptide solution). After at least 8 hours of incubation at 4° C. in the dark, ammonium chloride (50 mM) is added for two more hours to stop the reaction. Finally, the fluorescent peptide is purified by gel filtration (Sephadex G-10) using PBS.

The maleimide SMCC or SPDP-activated PNA/DNA is mixed with the sulfhydryl-fluorescent peptide in 100 mM sodium phosphate, 150 mM NaCl, (+1 mM EDTA for SPDP), pH 7.2 at the appropriate molar ratio. After an overnight incubation at room temperature, the final conjugate is isolated by gel filtration using Sephadex G-50. The fluorescence intensity of the final product relative to a standard curve allows quantification of the amount of peptide coupled to the DNA.

In a preferred embodiment, the SPDP approach, which leads to a disulficle bond between PNA and peptide, is used for peptides with fusogenic (endosomolytic) or targeting function. Once the peptides have performed their targeting or endosomal escape functions, they are cleaved from the DNA by the intracellular reducing environment. In contrast, the SMCC method is preferred for peptides containing a nuclear localization sequence because the peptide should remain attached to the DNA until it is delivered to the nucleus. These methods can be used to screen various unlabeled peptides for their ability to enhance reporter gene expression.

EXAMPLE 15

Peptide-PNA/DNA Gel Electrophoresis Analysis

This method is used to determine if the coupling reaction of the peptides affects electrophoretic mobility and integrity of the DNA and also confirms the presence of the coupled peptides if the DNA migration is affected by conjugation with the peptide which may depend on the overall charge of the peptide. Peptide-PNA/DNA is analyzed by electrophoresis on a 1% TAE agarose gel. Fluorescent peptide-PNA/DNA is visualized under ethidium bromide-free conditions and photographed under UV light. DNA integrity is analyzed by ethidium bromide staining.

EXAMPLE 16

Characterization of PNA/DNA Binding

The amount of peptide bound per plasmid is determined by independently measuring the DNA and peptide concentrations after the free peptide has been removed from the plasmid by gel filtration. The quantity of DNA recovered is determined by measuring the $OD_{260nm}$. If the peptide contains a fluorescent label, the amount of fluorescent peptide bound to the plasmid is determined using a standard curve of free fluorescent peptide. For peptides that do not contain a fluorescent tag, the fluorescamine assay is used to determine the amount of bound peptide. Purified plasmid without bound peptide does not give any background fluorescence in the fluorescamine assay. These measurements are used to determine the stoichiometry of peptide-PNA bound to plasmid DNA.

EXAMPLE 17

Nuclear Import Assay

Digitonin-permeabilized cells are a powerful system for studying the nuclear import of proteins (Adam et al., *J. Cell*

Biol. 111:807–816, 1990). This in vitro system allows nuclear uptake of plasmid to be directly monitored. The intranuclear uptake of plasmids containing various nuclear localization sequences is compared to plasmids lacking the bound peptide.

The nuclear import assay is performed essentially according to Adam et al. (supra.). Briefly, cells plated on coverslips are permeabilized for 5 min with 40 µg/ml digitonin (Molecular Probes) in transport buffer [(20 mM HEPES, pH 7.3., 110 mM potassium phosphate, 5 mM sodium acetate, 2 mM magnesium acetate, 0.5 mM EGTA, 2 mM DTT and 1 µg/ml each of aprotinin, pepstatin and leupeptin (Sigma)]. Coverslips are washed in transport buffer and inverted on a 100 µl drop of complete import mixture consisting of transport buffer plus 0.5 mM ATP, 0.2 mM GTP, 5 mM creatine phosphate, 1 unit creatine kinase (Calbiochem, San Diego, Calif.), 50% rabbit reticulocyte lysate (Promega) and fluorescently labeled DNA (with or without peptides). After various incubation times at 37° C., cells are washed with transport buffer, fixed with 2% formaldehyde for 30 minutes and mounted on slides in transport buffer containing 0.1% p-phenylenediamine dihydrochloride (Sigma). The nuclei are stained with DAPI or Hoechst 33258 dyes (Molecular Probes). Coverslips are mounted on slides and examined with an upright fluorescent microscope (Nikon, Eclipse E600) equipped with 60X oil immersion objective and a 3 CCD camera video system (Optronics). Images are captured using the Image-Pro Plus image analysis software (Media Cybernetics). As a control, fluorescent protein (BSA, dextran, allophycocyanin or streptavidin) coupled or not to nuclear localization peptides are used. The effect of some inhibitors of nuclear transport, including wheat germ agglutinin, temperature, energy depletion, antibody against nuclear pore complex and N-ethylmaleimide treatment, are also tested using this protocol.

EXAMPLE 18

DNA Stability Determination

DNA present in the import buffer after the nuclear import assay is extracted with phenol/chloroform/isoamyl alcohol, precipitated with isopropanol and washed with 70% ethanol. The DNA dissolved in water is analyzed on a 1% agarose gel. Cell fractionation (isolation of nuclei and cytoplasm) (Dingman et al., *Nucleic Acids Res.* 11:1475–1489, 1983) and extraction of peptide-PNA/DNA conjugates are performed according to standard procedures (Sambrook et al., *Molecular Cloning: A Laboratory Manual*, Cold Spring Harbor Laboratory Press, Cold spring Harbor, N.Y.). The stability of the DNA is analyzed by Southern blot with the DIG non-radioactive nucleic acid labeling and detection system.

EXAMPLE 19

Membrane Destabilization Assay

This in vitro system using a fluorophore encapsulated in liposomes allows the analysis of the activity of the fusogenic or membrane lytic peptides bound to the DNA. This assay is used to determine the quantity of coupled peptide required to lyse or to induce leakage of liposomes and to determine whether this activity is retained after binding the peptide to the plasmid. Functionality of several different peptides containing the lysis or fusogenic sequences and coupled to the DNA are analyzed. This leakage assay is a powerful system for studying the ability of peptides to fuse with membranes or to form pores in lipid bilayers (Wyman et al., *Biochemistry* 36:3008–3017, 1997; Parente et al., *Biochemistry* 29:8713–8719, 1990).

Reverse phase evaporation vesicles (liposomes) are prepared according to Szoka et al. (*Proc. Natl. Acad. Sci. U.S.A.* 75:4194–4198, 1978). Phospholipids (POPC: 1-palmitoyl-2-oleoyl-sn-glycero-3-phosphocholine and POPG: 1-palmitoyl-2-oleoylphosphatidylglycerol) are obtained from Avanti Polar Lipids (Birmingham, Ala.). The fluorophores 8-aminonaphthalene-1,2,3-trisulfonic acid (ANTS) and p-xylenebis(pyridinium) bromide (DPX) are obtained from Molecular Probes. Liposomes are made in 5 mM TES, 12.5 mM ANTS, 45 mM DPX and 20 mM KCl, pH 7.0, and extruded with an extruder (Liposofast, Avestin, Ottawa, Canada) through a 200 nm polycarbonate membrane. Non-encapsulated materials are removed by gel filtration (Sephadex G-75) with 5 mM TES and 100 mM KCl, pH 7.0.

The ANTS/DPX assay is used to monitor peptide-induced leakage of encapsulated ANTS from liposomes. This assay is performed according to Wynman et al. (supra.). Briefly, the fluorescence signal resulting from the quenching of ANTS released into the medium is measured with a spectrofluorometer (SPEX fluorolog). The excitation is set an 360 nm and the emission at 435 nm. Fluorescence intensity from intact liposomes ($F_0$) is set to 0% leakage and 100% leakage ($F_{100}$) obtained from complete lysis of the vesicles with C12E8 detergent (Calbiochem). The leakage extent of ANTS due to the peptides is determined using the following formula: % leakage=$(F-F_0)/(F_{100}-F_0)$, in which F represents the fluorescence intensity measured with the peptide.

EXAMPLE 20

Fluorescence Activated Cell Sorting (FACS) Analysis

FACS is used to detect fluorescent molecules delivered into cells or bound to the cell surface. This method is used to determine the specificity and functional activity of the coupled peptide that is recognized by a specific cell surface receptor. The specificity of binding is monitored using different cell lines and free peptides in standard competition assays. Analysis of cell surface bound peptides is performed according to Suzuki et al. (*Exp. Cell Res.* 193:112–119, 1991). Briefly, $2\times10^5$ cells are incubated with fluorescent peptide-PNA/DNA conjugate for 30 min at 4° C. Cells are washed extensively with cold PBS, fixed with 2% formaldehyde and analyzed by flow cytometry.

EXAMPLE 21

Biological Activity and Fluorescence Microscopy

In vitro transfection of peptide-PNA/DNA conjugate mediated by lipofection (cationic lipids) on several different cell lines (CV-1, B16 and NIH/3T3) is performed as described in Example 6. The level of reporter gene expression achieved with the peptide-PNA/DNA conjugate is compared to those obtained with the uncoupled DNA. The intracellular trafficking of fluorescent peptide-PNA/DNA conjugate tests the benefits of the coupled peptide on the level of DNA delivered and expressed in living cells and on the intracellular distribution (nuclear uptake) of plasmid DNA.

EXAMPLE 22

Activation of Transcription Using PNA-Peptide Complexes

Figure 8:
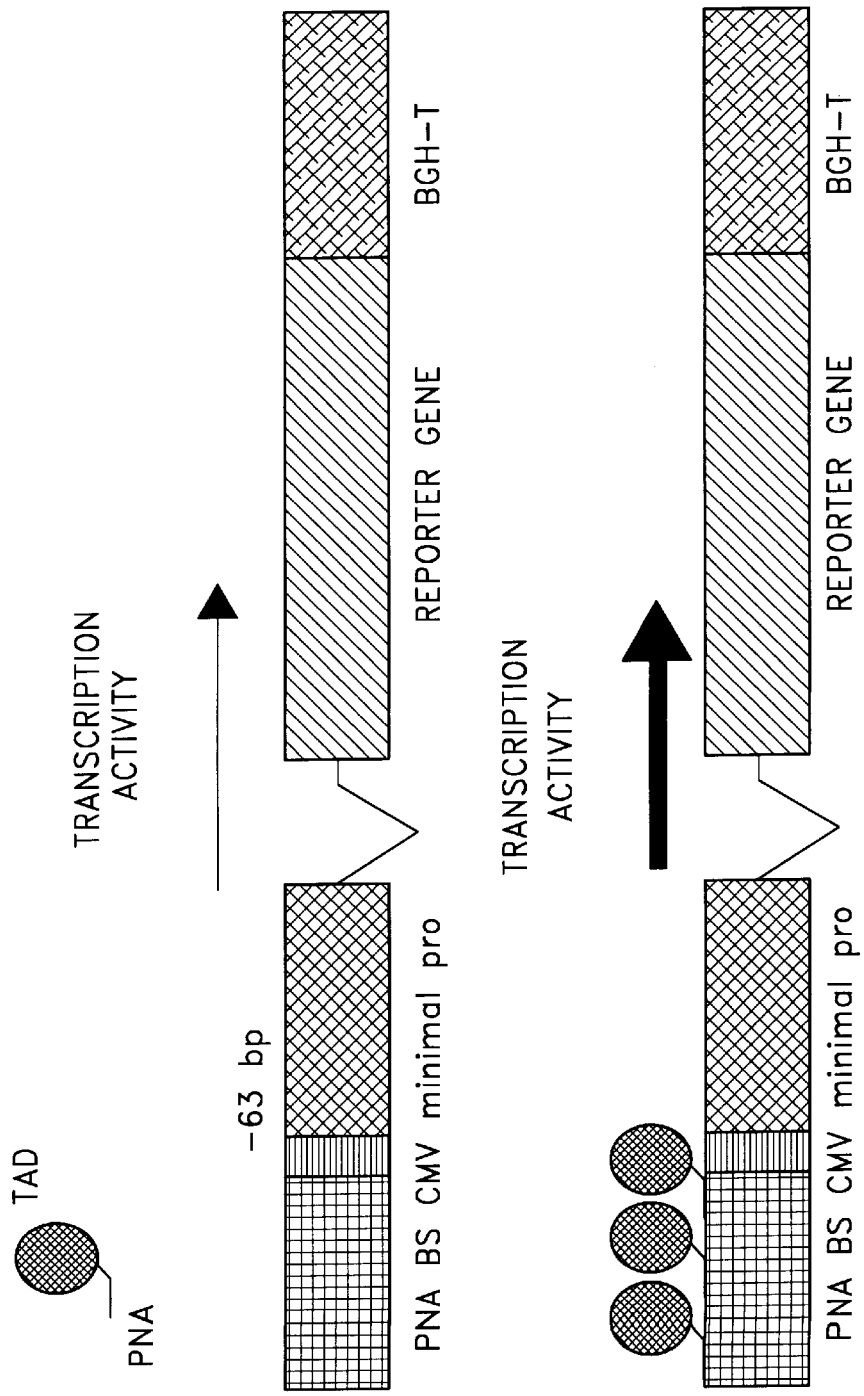
FIG. 8 illustrates the PNA approach for delivery of transcription activation domain peptides to the nucleus of transfected cells. These peptides (TAD) are linked to a plasmid via PNA to introduce artificial activators of transcription directly onto the plasmid.

Cytomegalovirus (CMV) immediate early (IE) promoter/enhancer is considered one of the strongest promoters active in a broad range of mammalian cells and tissues (Hartikka et al., *Human Gene Ther.* 7:1205–1217, 1996) due to a comprehensive array of enhancer elements located in a 600 base pair region upstream from its minimal promoter. FIG. 8 illustrates the PNA approach for delivery of transcription activation domains to the nucleus of transfected cells. These peptides are linked to a plasmid via PNA to introduce artificial activators of transcription directly onto the plasmid.

A CMV IE promoter-based plasmid is constructed which has PNA binding sites in place of the CMV IE enhancer using methods well known in the art. The transcription activity of this plasmid lacking the enhancer region is known to be very low (less than 3% of maximal expression), because it has only a minimal promoter and no ability to bind endogenous specific transcription factors (Gossen et al., *Proc. Natl. Acad. Sci. U.S.A.* 89:5547–5551, 1992). Peptides known to have specific transcription activating activity, such as the 437–447 amino acid peptide from herpes simplex virus VP16 (Seipel et al., supra.) are coupled to PNA using the method described in Example 12. The PNA-peptide conjugate is then hybridized to the plasmid as described in Example 2. In this way, a plasmid preparation is generated in which each plasmid molecule is capable of activating transcription regardless of the level of endogenous transcription factors.

Construction of plasmid—A DNA fragment of about 130 base pairs is generated by PCR using the primers 5'-GGATCCGCAAATGGGCGGTA-3' (SEQ ID NO:5) and 5'-CGGCCGCGGAGGCTGGA-3' (SEQ ID NO:6) and a human CMV IE promoter-based plasmid (Hartikka et al., supra.). The resulting PCR fragment contains the basic minimal promoter region from −63 to +70 bp flanked by EcoRI and SacII restriction sites. The enhancer region (−63 bp to −680) of the CMV IE gene promoter is then removed by cutting with MscI and SacII and replaced with the minimal promoter plus 6 PNA binding sites by ligating with EcoRI/SacII-cut above PCR fragment and an EcoRI-cut oligonucleotide having the sequence:

5' ATCTCTCTCTCTCTCTCTCTCTCTCTCTCTCTC TCTCTCTCTCTCTCTCGG TCCAG-3' (SEQ ID NO:7). A fully functional plasmid with high transcriptional activation potency is generated by hybridizing a chimeric molecule containing the PNA clamp covalently linked to a eukaryotic transcription activation domain to ithe PNA on the plasmid. The transcription activation peptide is evaluated by transfecting cells with the plasmid described above and shown in FIG. 8 having various bound PNA-peptide activators and comparing expressed reporter gene activity (e.g., β-galactosidase) with the results from transfection using a regular CMV IE promoter/enhancer-based plasmid (e.g., pPNA1-Lac Z).

While particular embodiments of the invention have been described in detail, it will be apparent to those skilled in the art that these embodiments are exemplary rather than limiting, and the true scope of the invention is that defined in the following claims.

What is claimed is:

1. A method for determining the biodistribution of an exogenous transfected nucleic acid molecule in a cell, comprising the steps of:
   contacting said exogenous nucleic acid molecule with a conjugated peptie nucleic acid (PNA) in a sequence-specific manner prior to transfection;
   transfecting said cell with said conjugated PNA; and
   monitoring the intracellular location of said nucleic acid molecule.

2. The method of claim 1, wherein said nucleic acid molecule is DNA or RNA.

3. The method of claim 1, wherein said PNA is conjugated to a fluorescent, calorimetric, radioactive or enzymatic label.

4. The method of claim 1, wherein said transfecting step is mediated by cationic lipids.

5. The method of claim 2, wherein said DNA is linear double stranded DNA, linear single stranded DNA, circular double stranded DNA or circular single stranded DNA.

6. The method of claim 2, wherein said DNA molecule is a plasmid.

7. A kit, comprising:
   a DNA molecule comprising a PNA binding site and a multiple cloning site for insertion of a nucleic acid sequence;
   a PNA conjugate which binds to said PNA binding site; and
   sequencing primers complementary to said multiple cloning site.

8. The kit of claim 7, wherein said DNA molecule is a plasmid.

9. The kit of claim 7, further comprising labeling buffer.

10. The kit of claim 7, wherein said PNA is conjugated to a fluorescent label.

11. The kit of claim 7, wherein said PNA is conjugated to a chemical group which reacts with a chemical group on a protein.

12. The kit of claim 11, wherein said chemical group is pyridyldithiol or maleimide.

13. A composition comprising a plasmid and a conjugated PNA molecule associated with said plasmid, wherein said PNA molecule contains a region complementary to said plasmid.

14. The composition of claim 13, wherein said plasmid encodes a reporter gene or therapeutic gene.

15. The composition of claim 13, wherein said PNA is conjugated to a fluorescent, colorimetric, radioactive or enzymatic label.

16. The composition of claim 13, wherein said PNA is conjugated to a protein, peptide, carbohydrate moiety or receptor ligand.

17. The composition of claim 14, wherein said reporter gene is selected from the group consisting of β-galactosidase, luciferase, chloramphenicol acetyltransferase, green fluorescence protein and secreted alkaline phosphatase.

18. The composition of claim 14, wherein said therapeutic gene is selected from the group consisting of cystic fibrosis transmembrane receptor (CFTR), insulin, dystrophin, interleukin-2, interleukin-12, erythropoietin, gamma interferon and granulocyte macrophage colony stimulating factor.

19. The composition of claim 16, wherein said peptide is selected from the group consisting of a nuclear localization signal peptide, an endosomal lytic peptide, a transcriptional activator domain peptide, a receptor specific peptide and an immunostimulatory peptide.

20. A composition comprising a nucleic acid molecule and a conjugated PNA molecule associated with said nucleic acid molecule, wherein said PNA molecule is conjugated to a moiety selected from the group consisting of a colorimetric label, radioactive label, enzymatic label, peptide which enhances transfection and/or expression of said nucleic acid molecule, immunostimulatory peptide, carbohydrate moiety and receptor ligand, wherein said PNA molecule contains a region complementary to said nucleic acid molecule.

21. The composition of claim 20, wherein said nucleic acid molecule is DNA or RNA.

22. The composition of claim 20, wherein said peptide which enhances transfection and/or expression of said nucleic acid molecule is selected from the group consisting of a nuclear localization signal peptide, an endosomal lytic peptide, a transcriptional activator domain peptide, a receptor specific peptide.

23. The composition of claim 21, wherein said DNA molecule is selected from the group consisting of linear double stranded DNA, linear single stranded DNA, circular double stranded DNA and circular single stranded DNA.

24. The composition of claim 21, wherein said DNA molecule is a plasmid.

25. The composition of claim 24, wherein said plasmid encodes a reporter gene or therapeutic gene.

26. The composition of claim 25, wherein said reporter gene is selected from the group consisting of β-galactosidase, luciferase, chloramphenicol acetyltransferase, green fluorescence protein and secreted alkaline phosphatase.

27. The composition of claim 25, wherein said therapeutic gene is selected from the group consisting of cystic fibrosis transmembrane regulator (CFTR), insulin, dystrophin, interleukin-2, interleukin-12, erythropoietin, gamma interferon and granulocyte macrophage colony stimulating factor.

* * * * *